(12) United States Patent
Marangoni

(10) Patent No.: US 12,324,800 B2
(45) Date of Patent: Jun. 10, 2025

(54) LECITHIN VESICLES

(71) Applicant: CannaClear Inc., Whistler (CA)

(72) Inventor: Alejandro Marangoni, Guelph (CA)

(73) Assignee: CANNACLEAR INC., Whistler (CA)

( * ) Notice: Subject to any disclaimer, the term of this patent is extended or adjusted under 35 U.S.C. 154(b) by 779 days.

(21) Appl. No.: 17/425,149

(22) PCT Filed: Jan. 24, 2020

(86) PCT No.: PCT/CA2020/050086
§ 371 (c)(1),
(2) Date: Jul. 22, 2021

(87) PCT Pub. No.: WO2020/150834
PCT Pub. Date: Jul. 30, 2020

(65) Prior Publication Data
US 2022/0117932 A1  Apr. 21, 2022

Related U.S. Application Data

(63) Continuation-in-part of application No. 16/256,594, filed on Jan. 24, 2019, now Pat. No. 11,154,502.

(51) Int. Cl.
| | | |
|---|---|---|
| *A61K 31/352* | (2006.01) | |
| *A61K 9/127* | (2006.01) | |
| *A61K 31/01* | (2006.01) | |
| *A61K 31/015* | (2006.01) | |
| *A61K 31/045* | (2006.01) | |
| *A61K 31/05* | (2006.01) | |
| *A61K 47/24* | (2006.01) | |

(52) U.S. Cl.
CPC ............ *A61K 31/352* (2013.01); *A61K 9/127* (2013.01); *A61K 31/01* (2013.01); *A61K 31/015* (2013.01); *A61K 31/045* (2013.01); *A61K 31/05* (2013.01); *A61K 47/24* (2013.01)

(58) Field of Classification Search
None
See application file for complete search history.

(56) References Cited

U.S. PATENT DOCUMENTS

| | | |
|---|---|---|
| 4,532,089 A | 7/1985 | MacDonald et al. |
| 5,173,219 A | 12/1992 | Kim |
| 5,185,154 A | 2/1993 | Lasic et al. |
| 6,312,719 B1 | 11/2001 | Hope |
| 6,855,277 B2 | 2/2005 | Baker |
| 8,808,734 B2 | 8/2014 | Winnicki |
| 10,052,303 B2 | 8/2018 | Winnicki |
| 2010/0086573 A1* | 4/2010 | Anderson ............ A61K 8/678 424/401 |
| 2011/0318406 A1 | 12/2011 | Eley et al. |
| 2016/0030387 A1* | 2/2016 | Winnicki ............ A61K 47/24 514/454 |
| 2018/0344786 A1 | 12/2018 | Thacker, Jr. |
| 2022/0071198 A1* | 3/2022 | Eley ........................ A01N 37/14 |

FOREIGN PATENT DOCUMENTS

| | | |
|---|---|---|
| CA | 2461702 | 4/2003 |
| EP | 3632410 | 8/2020 |
| WO | 2011115684 | 9/2011 |
| WO | 2015068052 | 5/2015 |

OTHER PUBLICATIONS

International Search Report—PCT/CA2020/05086 dated Feb. 28, 2020.
Sandeep Kalepu et al.—"Liposomal drug delivery system: A comprehensive review", Int. J. Dev. & Res.; Oct.-Dec. 2013, vol. 5, Issue 4, pp. 62-75, the whole document.
H. H. Hub et al.—"Preparation of large unilamellar vesicles", FEBS letters; Apr. 1982; vol. 140, pp. 254-256, the whole document.
Hiroshi Kikushi et al.—"A polyol dilution method for mass production of liposomes", Journal of Liposome Research; 1994, vol. 4, No. 1; pp. 71-91, the whole document.
Ayelet Barenholz et al.—"Nano-Liposome of crude soy lecithin are effective for cleaning fuel-contaminated sand and soils", Expert Opinion on Environmental Biology; Jul. 11, 2016; vol. 5, No. 3; pp. 1-6, the whole document.
M. J. Hope et al.—"Generation of multiamellar and unilamellar phospholipid vesicles", Chemistry and Physics of Lipids; 1986; vol. 40; pp. 89-107, the whole document.
Chandraprakash Dwivedi et al.—"Review on preparation and characterization of liposomes with application", Journal of Scientific & Innovative Research; Mar.-Apr. 2013; vol. 2, No. 2; pp. 486-508.
Ateeq Rahman et al.—"Mini review on emerging methods of preparation of liposome and its application as liposome drug delivery systems", Open Journal of Pharmacology and Pharmacotherapeutics; Oct. 26, 2018; pp. 5-21.
Marin C. Woddle et al.—"Liposome preparation and size characterization", Methods Enzymol, 1989, vol. 171, pp. 193-217.
Francis Szoka et al.—"Comparative properties and methods of preparation of lipid vesicles (liposomes)", Am. Rev. Biophys. Bioeng.; 1980, vol. 9; pp. 467-508.
Adriano Rodrigues Machado et al.—"Importance of lecithin for encapsulation processes", African Journal of Food Science, Apr. 2014, vol. 8, No. 4; pp. 176-183.
Bansal et al.—"Feasibility study of lecithin nanovesicles as spacers to improve the solubility of milk protein concentrate powder during storage", Dairy Sci. & Technol. (2017) 96: 861-872.

(Continued)

*Primary Examiner* — Celeste A Roney
(74) *Attorney, Agent, or Firm* — Gowling WLG (Canada) LLP

(57) ABSTRACT

Giant multi-lamellar vesicles (GMVs) comprising lecithin are provided which are about 3 to about 15 μm in size. Methods for preparing the GMVs, and for preparing large unilamellar vesicles (LUVs) from the GMVs, are provided, as well as methods for encapsulating cargo within the GMVs and LUVs. The present vesicles are useful for the oral delivery of encapsulated cargo.

18 Claims, 21 Drawing Sheets

(56) References Cited

OTHER PUBLICATIONS

Delarco et al.—Paradoxical roles for antioxidants in tumor prevention and eradication:, Cancer Biology and Therapy, 2020, 9(5), 362-370.
Whitehurst et al.—Emulsifiers in Food Technology, Lecithins, Blackwell Publishing, 2004.

* cited by examiner

A)

B)

FIGURE 23 - Continued
D)
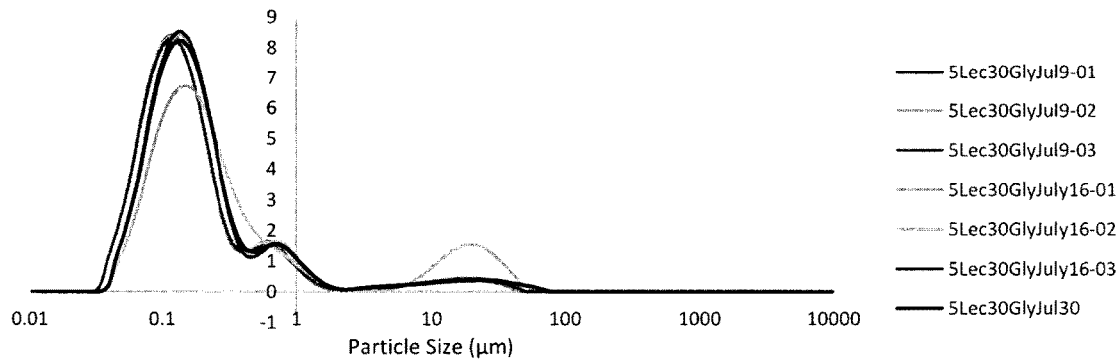
E)
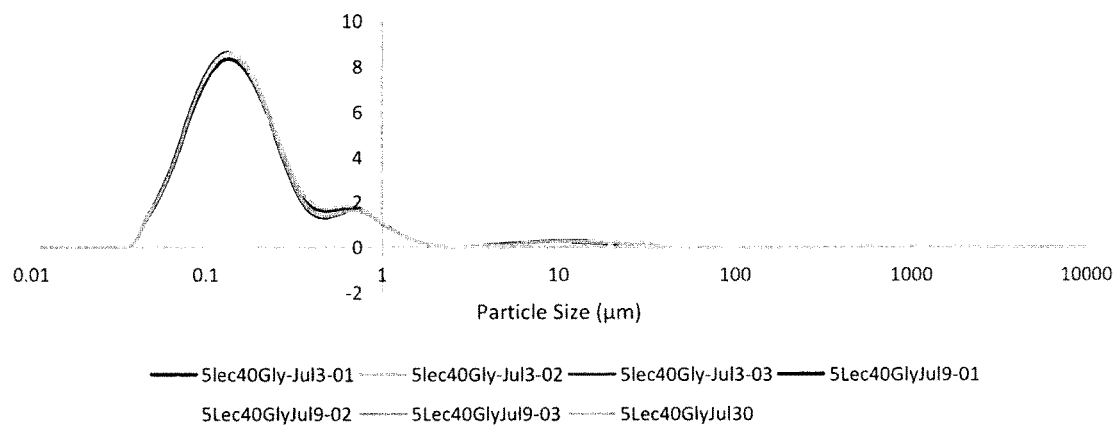
F)
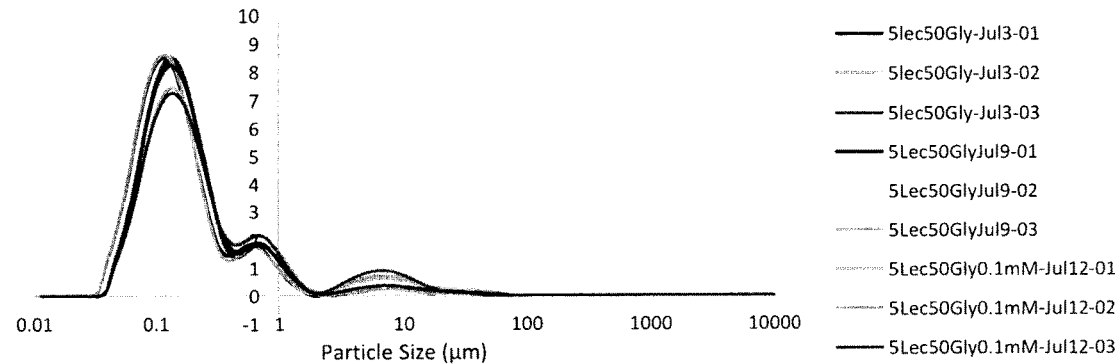

FIGURE 23 - Continued
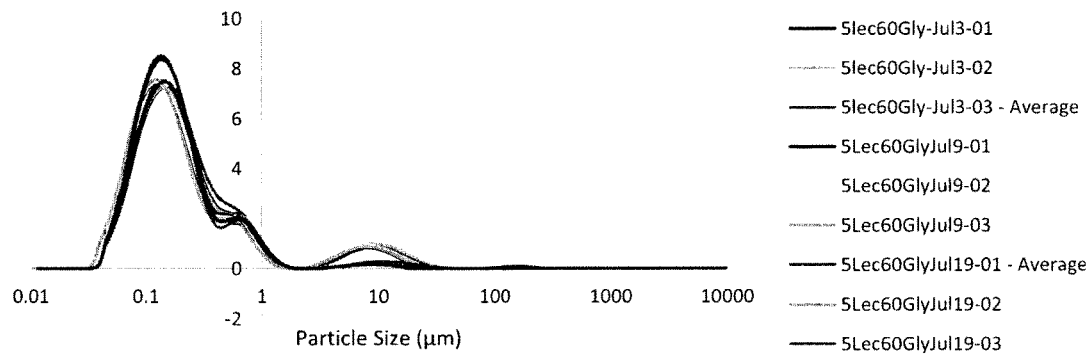
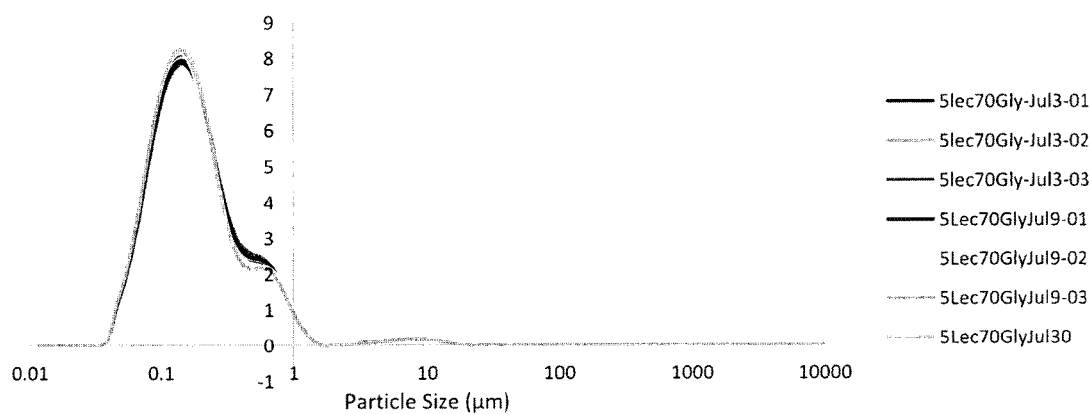
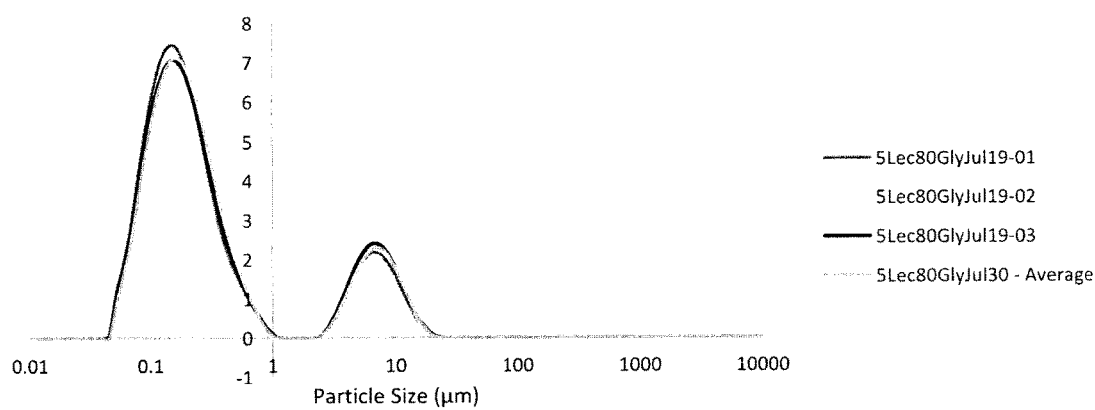

FIGURE 23 - Continued
J)
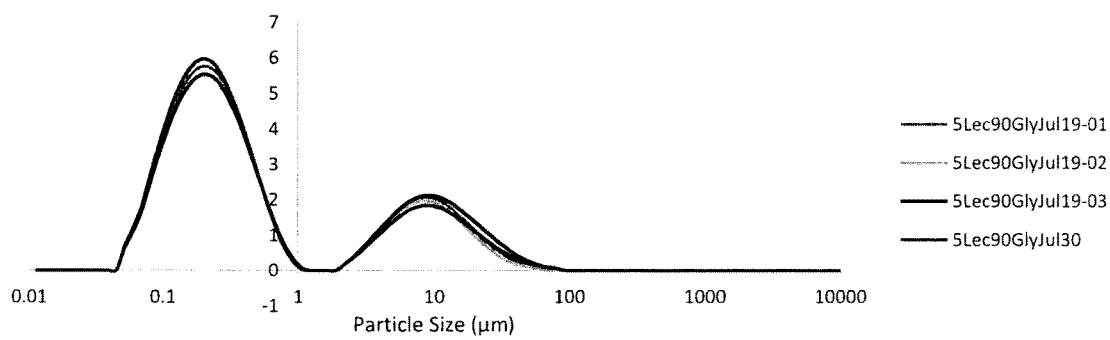
K)
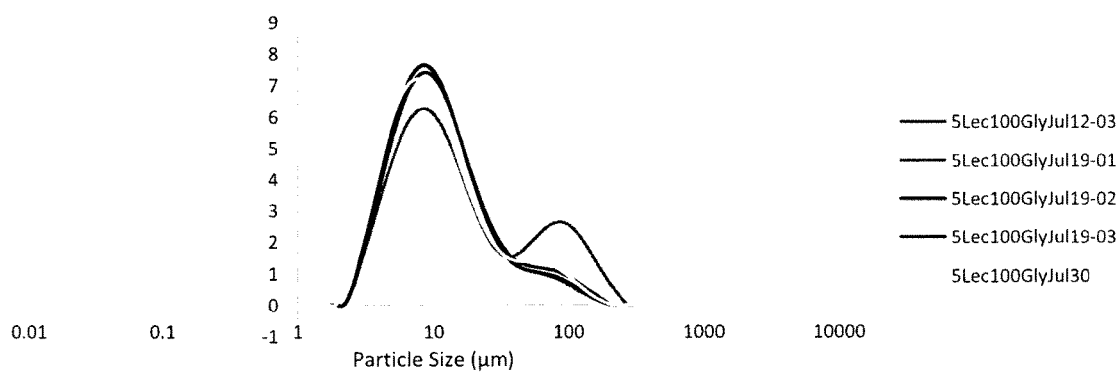

LECITHIN VESICLES

FIELD OF THE INVENTION

The present invention generally relates to vesicles prepared from lecithin, and in particular relates to vesicles useful for encapsulation of cargo for oral and other forms of administration.

BACKGROUND OF THE INVENTION

Phospholipid bilayer vesicles have a long history of use as bioactive delivery systems. Phospholipids are the natural building blocks of all biological membranes in nature, the outer layer of cells and subcellular organelles. Phospholipids are amphipathic (or amphiphilic) molecules which contain hydrophobic and hydrophilic parts. When exposed to either hydrophobic or hydrophilic environments, these molecules associate with each other such that hydrophilic or water-loving regions associate with other such regions, and hydrophobic or water-hating regions associate with other such regions. This molecular "phase separation" is the driving force for self-assembly and eventual supramolecular structure formation. Most phospholipids when dispersed/dissolved in water, self-assemble into bilayers, effectively creating a two-dimensional fluid where molecules display translational, rotational and transverse (flip-flop across monolayers) motions. These bilayers very seldom remain in an open and planar arrangement due to the high energy costs of the edges exposed to water, and thus tend to naturally close to form phospholipid vesicles.

As opposed to emulsions or micelles, these vesicles have a central watery lumen since they are effectively closed bilayers as shown in FIG. 1A. Artificially constructed phospholipid bilayer vesicles are referred to as liposomes. Interest in liposomes arises due to their ability to: i) encapsulate or entrap both hydrophilic and hydrophobic bioactive compounds (drugs, nutraceuticals, cosmeceuticals), ii) cross cell membranes; and iii) transport these bioactive compounds to specific, even targeted, locations within the human body. Hydrophobic compounds can be incorporated within the hydrophobic aliphatic fatty acid chains of the phospholipids, while hydrophilic compounds can be incorporated in the watery lumen of the liposome. Liposomes differ from micelles, which are also spherical structures, but which are instead composed of a monolayer of an amphiphile. Phospholipids usually do not form micelles, but lysophospholipids and fatty acids do form micelles.

Liposomes can be classified according to their size and lamellarity, i.e. the number of bilayers present in the liposome as shown in FIG. 1B. Liposomes usually range from 20 nm to 1000 nm (1 μm) in diameter. Within this range, further size categories are identified as set out in Table 1.

TABLE 1

Current classification of phospholipid vesicles according to size and lamellarity.

| Liposome Types | Size | Number of Lamellae |
|---|---|---|
| Small Unilamellar Vesicles (SUV) | 20 nm-100 nm | Single |
| Multivesicular Vesicles (MW) | 200 nm-~3 μm | Multiple |
| Large Unilamellar Vesicles (LUV) | 100 nm-400 nm | Single |
| Large Multilamellar Vesicles (MLV) | 200 nm-~3 μm | Multiple |
| Giant Unilamellar Vesicles (GUV) | 1 μm and Larger | Single |

Liposomes are frequently manufactured by first dissolving phospholipids in an organic solvent, such as chloroform, chloroform-methanol or even ethanol, depending on the type of phospholipid used. A clear lipid film is subsequently formed by removal of the solvent, and gentle hydration of this film eventually leads to formation of large, multilamellar vesicles (MLV). An MLV consists of more than one bi layer, e.g. concentric bilayers, creating a structure analogous to that of an onion. Each bilayer is separated from the next by water. SUVs are produced by disrupting MLVs or MVVs using membrane filtration, sonication (agitation by soundwaves), pH jump techniques, and possibly micro fluidization. These high energy processes can yield predominantly LUVs and some SUVs. However, the SUVs are not stable for long periods of lime without addition of specific stabilizers and will lend to form larger vesicles (LUVs). Storing SUVs at a temperature above their gel to liquid-crystalline phase transition temperature can help prevent formation of larger vesicles. This can be achieved most easily by selecting phospholipids that are unsaturated rather than saturated. To produce LUVs, extrusion through defined-pore size polycarbonate filters and microfluidization is used, following several freeze-thaw cycles, an MLV or MVV phospholipid suspension is forced through polycarbonate filters at high pressures and temperatures above the gel to liquid-crystalline phase transition temperature, leading to the formation of liposomes with diameters similar to the size of the pores they were extruded through. This technique, if employed with pores of approximately 100 nm in diameter, allows for the formation of LUVs approximately 120 nm-140 nm in size. The size distribution achieved by this method is much more reproducible and narrower than that achieved through sonication. More modern disruption techniques include the use of high-pressure homogenizers, such as microfluidizers, where vesicles are passed 3-4 times through interaction chambers at pressures upwards of 30,000 PSI. Vesicles in the size range 70-150 nm can be achieved in this fashion.

Liposomes have largely been used by the pharmaceutical industry for drug delivery. Decreased drug toxicity, increased drug stability and targeted delivery are some of the main advantages of thus encapsulation and delivery strategy. The useful size range of these structures for medical applications is between 50 nm and 250 nm, particularly for intravenous drug delivery. When injected into the circulatory system, liposome clearance is determined by the rale and extent of both drug release and uptake of liposomes by cells of the mononuclear phagocyte system (MPS), or reticuloendothelial system (RES). It has been reported that liposomes smaller than 100 nm interact less with plasma proteins, evade capture by the RES, have a longer half-life in the blood, and accumulate passively at tumoral sites. Conversely, it was found that larger liposomes were eliminated more rapidly from blood circulation and do not escape RES uptake. Besides the requirement for small liposome sizes, the pharmaceutical industry requires well-defined molecular structures and compositions. For this reason, phospholipids used in these applications are preferably highly purified and molecularly homogenous, rather than being natural mixtures extracted from whole tissue such as dipalmitoyl-phosphatidylcholine or egg phosphatidylcholine.

In the frenzy of creating smaller and smaller liposomes for intravenous medical applications and targeted delivery, for example, to tumors or specific tissues, the utility of multilamellar vesicles discovered by Alex Bangham has not fully been considered. While some elegant studies were conducted in the late 1980's to address the mechanism of liposome formation, the research did not progress past a certain point. A question that arose during this period was whether phospholipid vesicles could form spontaneously and whether liposomes could be considered thermodynamically stable. This thermodynamic stability would differentiate them from oil-in-water emulsions, which are kinetically stable, but not thermodynamically stable.

While size and purity are important for pharmaceutical-grade liposomes, liposome characteristics required for oral delivery are not as stringent, particularly in foods. Liposomes are usually destroyed once they reach or exit the stomach and enter the small intestine. The harsh acidic environment and shear in the stomach, and the bile salts and enzymatic attack in the small intestine, are no match for a liposome. The liposome and its contents are integrated into the digestive system structures at this point. The size of the liposome, thus, is not as important in this case. Moreover, since these liposomes are used as food, there is no need to use high purity phospholipids for this application.

Although liposomes may be prepared with several polar lipid combinations, most work has been done with phosphatidylcholine. The mason for the popularity of phosphatidylcholine is because it is easy to solvent-fractionate from other phospholipids (ethanol-soluble) and purify, it is the most abundant phospholipid in biological membranes, and it forms stable liposomes readily and reproducibly. Moreover, the saturated versions of this phospholipid are preferred due to their oxidative stability and tendency to form lamellar mesophases, which are the core structure in a phospholipid bilayer. A drawback, however, is its high cost.

Interestingly, no natural system contains only phosphatidylcholine. Biological membranes are composed of complex mixtures of large numbers of polar lipids and proteins. Lecithin is technically a natural mixture of phospholipids extracted from biological tissue. For example, many plant membranes contain equal amounts of phosphatidylcholine, phosphatidylethanolamine and phosphatidylinositol. Other commonly found phospholipids include the single-chain version of the different phospholipids, the lyso-phosphatides, as well as phosphatidic acid. However, lecithin is often equated with only the phosphatidylcholine component of membranes.

In view of the foregoing, it would be desirable to develop a novel liposome or vesicle designed for oral delivery.

SUMMARY OF THE INVENTION

Novel multi-lamellar vesicles comprising lecithin have now been developed which are suitable for use to orally deliver cargo.

Accordingly, in one aspect of the invention, multi-lamellar vesicles comprising lecithin are provided which are greater than 3 μm in size.

In another aspect, a method of preparing multi-lamellar vesicles which are greater than 3 μm in size is provided comprising the step of mixing lecithin in a buffer until fully dispersed.

In another aspect, a method of preparing large unilamellar vesicles is provided comprising the step of exposing multi-lamellar vesicles comprising lecithin which are greater than 3 μm in size to mixing for a sufficient period of time.

In another aspect, large unilamellar vesicles having a size in the range of about 100-400 nm are provided consisting essentially of lecithin.

In a further aspect, a method of reducing the size of giant vesicles is provided comprising the step of mixing the giant vesicles with a low molecular weight polyol for a sufficient period of lime.

These and other aspects of the invention will become apparent from the detailed description that follows by reference to the following figures.

DETAILED DESCRIPTION OF THE INVENTION

Figure 1:
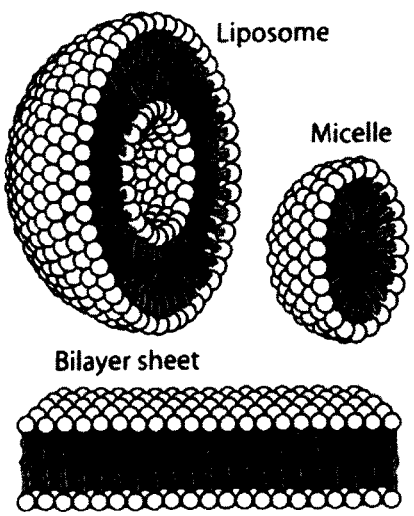
FIG. 1 is a schematic illustrating a liposome, micelle and phospholipid bilayer (A), and various types of liposomes according to size and lamellarity (B)
Figure 1:
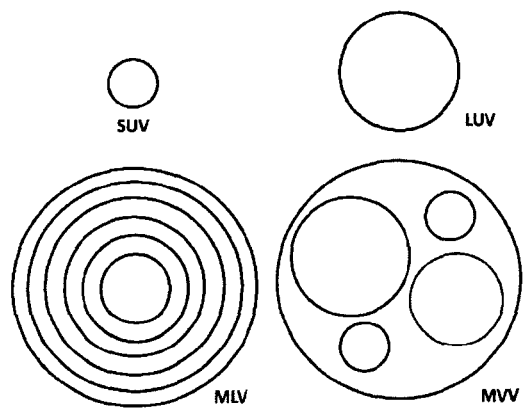

Multi-lamellar vesicles comprising lecithin are provided which are greater than 3 μm in size, e.g. referred to herein as giant multi-lamellar vesicles or GMVs.

The vesicles are made of lecithin which comprises a mixture of glycerophospholipids including, for example, one or more of a phosphatidylcholine, phosphatidyl-ethanolamine, phosphatidylinositol, phosphatidylserine and phosphatidic acid. Examples of glycerophospholipids in lecithin include, but are not limited to, dilinoleylphosphatidylcholine, dilinoleylphosphatidylethanolmine, dilinoleylphosphatidylinositol, dilinoleylphosphatidylserine, dilinoleylphosphatidic acid, dioleylphosphatidylcholine, dioleylphosphalidylethanolamine, diloleylphosphatidylinositol, dioleylphosphatidylserine, dioleylphosphatidic acid, 1-oleyl-2-linoleylphosphatidylcholine, 1-oleyl-2-linoleylphosphatidyl-ethanolamine, 1-oleyl-2-linoleylphosphatidylinositol, 1-oleyl-2-linoleylphosphatidylserine, 1-oleyl-2-linoleylphosphatidic acid, dipalmitoylphosphatidylcholine, dipalmitoylphosphatidylethanolamine, dipalmitoylphosphatidylionsitol, dipalmitoylphosphatidylserine, dipalmitoylphosphatidic acid, combinations of linolenic, linoleic, oleic, palmitic, stearic fatty, behenic, crude, myristic, lauric, capric, caproic and caprylic fatty acids at positions sn-1 and sn-2 on each different phospholipid backbone (i.e. on the backbone of phosphatidylcholine, phosphatidylethanolamine, phosphatidylinositol, phosphatidylserine and phosphatidic add). The lecithin may also include small amounts of glycolipids, carbohydrates and/or sterols.

In one embodiment, the lecithin comprises at least a phosphatidylcholine and a phosphatidylethanolamine in which the phosphatidylcholine to phosphatidylethanolamine (PC:PE) ratio is 1:1 to 10:1 PC:PE, preferably 1:1 to 5:1 PC:PE, such as 1:1 to 2:1 PC:PE, and more preferably the PC:PE ratio is greater than 1 or greater than or equal to 1.5 (e.g. PC>PE). In addition, the lecithin comprises less than 10 wt % of phosphatidic acid and less than 5% lysophosphatides, and preferably comprises less than 5 wt % phosphatidic acid and lysophosphatides combined, or no significant amount of phosphatidic acid and lysophosphatides, i.e. less than 1 wt %. Both phosphatidic acid and lysophosphatides are by-products of phospholipid degradation and have deleterious effects on phospholipid bilayer stability. Lysophosphatides are strong micellar phase formers while phosphatidic acid has a strong tendency to bind to metals, such as calcium, and form insoluble complexes. Thus, lecithin for use to prepare GMVs may comprise phosphatidylcholine in an amount in the range of about 15-80 wt % phosphatidylcholine, preferably 25-65 wt % phosphatidylcholine, and about 10-25 wt % phosphatidylethanolamine, preferably 10-15 wt % phosphatidylethanolamine.

The fatty acid content of the lecithin also contributes to the properties of the lecithin. Preferred fatty acids within the lecithin include fatty acids with 16 and 18 carbon chains, such as saturated or monounsaturated laity acids such as oleic and linoleic acid, while polyunsaturated fatty acids such as linolenic acid are not desirable. Preferably, the fatty acid content of the lecithin comprises greater than 60% by wt oleic and linoleic acid combined, and more preferably greater than 70%, 75% or 80% by wt oleic and linoleic acid, while comprising 15% or less of linolenic acid, e.g. less than 10%.

Sources of lecithin for use to prepare the present vesicles is not particularly limited. Suitable sources include, but are not limited to, egg yolk, and vegetable sources, e.g. oilseeds such as sunflower, soybean, nuts and whole grains. Preferable are lecithins from vegetable sources, and most preferable are organically sourced lecithins. Lecithin is readily commercially available.

The present vesicles are prepared by mixing lecithin in an aqueous buffer until fully dispersed. The lecithin is dispersed in the buffer in an amount in the range of about 2-20% (w/w), preferably 5-15% (w/w) such as 10% (w/w). Generally, the lecithin dissolves in the buffer with mixing for at least about 15-60 minutes at a selected temperature, e.g. ranging from about 4° C. to about 75° C., preferably around 40-50° C., which enhances hydration and prevents microbial growth. Examples of suitable buffers include acidic, basic or neutral buffers which exhibit high water solubility and minimal organic solvent solubility, exclusion by cellular membranes, minimal salt interactions and minimal interactions between buffer and reaction components, stable and resistant to enzymatic degradation, and exhibit minimal changes on dissociation from changes in concentration and temperature. Thus, suitable buffers include, but are not limited to, phosphate, citrate, malate, or other suitable biological buffer as would be known by one of skill in the art. Buffer may be used in a concentration range of 0.01-0.1 M.

In one embodiment, an acidic buffer is used to dissolve the lecithin which advantageously provides the vesicles with microbial stability. Acidic buffer will generally comprise a weak acid, such as citric acid, ethanoic or acetic acid, lactic acid or phosphoric acid, and a salt of the acid, e.g. a sodium or potassium salt. The pH of the acidic buffer will be a pH that is greater than or equal to the pK of the phosphate group of the phospholipid within the lecithin, or a pH at which there is electrostatic stabilization of the mixture against flocculation and coalescence. Thus, the pH may be less than the pK of the phosphate of a phosphatidylcholine or phosphatidylethanolamine since these have a charged quaternary amine or protonated primary amine, respectively, which provides the necessary electrostatic stabilization. Preferably, the pH of the buffer is less than 6, but greater than 2.5, and more, preferably the pH is about 3-5.

The resulting multi-lamellar vesicles, or GMVs, thus, consist essentially of lecithin, and are greater than 3 μm in size, preferably between 4 to 15 μm in size, and more preferably, 5 to 12 μm in size, such as greater than 5 μm in size and less than 10 μm in size. The present vesicles, thus, prepared by admixture of lecithin with a buffer, provide a relatively uniform population of GMVs, which are advantageously stable in a liquid crystalline state over a temperature range of 0-90° C.

The present vesicles may be modified to incorporate water soluble or fat soluble cargo. Water soluble cargo is entrapped in the lumen of the vesicles, while fat soluble cargo is captured in the vesicle membrane. Thus, the vesicles are useful to deliver a various types of cargo, from small molecule to macromolecule such as proteins, nucleic acids (DNA or RNA), hormones, polysaccharides, glycoproteins, tocopherols, sterols, phytosterols, phytosterol esters, cholesterol and other naturally occurring or synthetic small or macromolecules, including both hydrophilic or hydrophobic molecules.

The vesicles may include a load equivalent to a mass ratio of the selected cargo to lecithin of 1:99 to 1:4 (w/w), preferably 1:50 to 1:5 (w/w) cargo to lecithin, e.g. 1:20, 1:19 or 1:18 to 1:8, 1:9 or 1:10.

In one embodiment, the vesicles are modified to incorporate one or more cannabinoids. Examples include, but are not limited to, cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), cannabidivarin acid (CBDVA), cannabinovarin (CBNV), cannabinodiol (CBDL), cannabicyclol (CBL), cannabielsoin (CBE), cannabitriol (CBT), cannabivarin (CBV), cannabichromevarin (CBCV), cannabigerol monoethyl ether (CBGM), tetrahydrocannabinols (THC), tetrahydrocannabivarin (THCV), naphthoylindoles such as JWH-018, JWH-073, JWH-398, JWH-200, JWH-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenols such as CP 47,497-C8 and CP 47,497; HU-210; terpenes (e.g. myrcene, beta caryophyllene, pinene, limonene, terpinolene, humulene, nerolidol, linalool, ocimene, guaiol, bisabolol, alpha phellandrene, cadinene, camphene, camphor, citral, citronellol, delta 3-carene, eucalyptol, eugenol, gamma terpinene, geraniol, humulene, nerol, nerolidol, ocimene, para-cymene, phytol, pulegone, terpineol and valencene) and pharmaceutically acceptable salts thereof.

In another embodiment, the vesicles are modified to incorporate a water soluble cannabinoid within the lumen thereof. For example, the vesicles may incorporate a natural carboxylated cannabinoid. Alternatively, the vesicles may incorporate a glycosylated cannabinoid.

For cargo that is susceptible to oxidation, such as cannabinoids, it may be desirable for the vesicles to also include an antioxidant. In one embodiment, a phenolic antioxidant is used. Non-limiting examples of suitable phenolic antioxidants are tert-butyl hydroxy quinone (TBHQ), butylated hydroxy toluene (BHT), butylated hydroxyl anisole (BHA), propyl gallate (PG), a tocopherol and mixtures thereof. For water-soluble cannabinoids entrapped within the lumen of the liposome, water soluble antioxidants such as ascorbic or erythorbic acid may be utilized to increase stability.

Vesicles incorporating selected cargo may be prepared by the following techniques. The cargo may be dissolved in a solvent, combined in a drip-wise manner with lecithin dispersed in a buffer (e.g. already formed vesicles, i.e. GMVs) and then mixed for a period of time sufficient for uptake of the cargo by the vesicles. This technique is generally used for hydrophobic cargo such as cannabinoids, which may be dissolved in a solvent such as an alcohol, e.g. ethanol, propanol or butanol, or a stronger organic solvent such as chloroform, if required (e.g. for lipophilic cargo). The dissolved hydrophobic cargo solution is then combined with the vesicles. The cargo solution is generally added very slowly, e.g. a drop at a time, to the vesicle mixture to entrap the hydrophobic cargo within the phospholipid bilayers of the vesicle and to prevent the formation of undesirable aggregates. The method is generally conducted at increased temperature to facilitate cargo incorporation, for example, a temperature in the range of between 55-75° C., e.g. 60-70° C., and to facilitate evaporation of unwanted solvent from the resulting product.

For water soluble cargo (e.g. such as water-soluble cannabinoids), these may be dissolved in an aqueous solvent, e.g. buffer, which is then combined with the lecithin to yield vesicles (GMV) encapsulating the water-soluble cargo. Following mixing and uptake of the cargo into the vesicle lumen, entrapment of the cargo may be enhanced by repeated freeze-thaw cycles followed by homogenization, membrane filtration, sonication or pH Jump.

In another embodiment, novel large unilamellar vesicles (LUVs) comprising lecithin may be prepared. LUVs are about 100-400 nm in size. LUVs may be prepared by exposing the present giant multi-lamellar vesicles (GMVs) to mixing (including by circulation through a rotostator, shear pump, or similar device) for example, at 10,000-25,000 rpm tor a period of time to shear GMVs to yield LUVs. As one of skill in the art will appreciate, the greater the rate of mixing, the less time required to form LUVs. Thus, using a mixing rate of 20,000-25,000 rpm, LUVs can be prepared from GMVs within about 15 minutes or less, e.g. 5 minutes. Using a mixing rate of 10,000 rpm increases the time to yield LUVs, e.g. 30-60 minutes. In one embodiment, rotor-stator mixing may be used to form the LUVs from the GMVs at various rpm.

The present LUVs comprising cargo may also be prepared. For hydrophobic cargo, the selected cargo is dissolved in an appropriate solvent as described above. The dissolved cargo may be combined in a dropwise manner with GMVs and then subjected to mixing as above to form cargo-containing LUVs. Alternatively, the dissolved hydrophobic cargo may be added very slowly (e.g. a drop at a time) with mixing to already formed LUVs to form cargo-containing LUVs. For hydrophilic cargo, the selected cargo may be combined with buffer and then mixed with lecithin to form cargo-containing GMVs which are then subjected to the required mixing to form cargo-containing LUVs.

Combining the cargo with GMVs or LUVs may be conducted at increased temperature, for example, a temperature in the range of between 55-75° C., in order to facilitate incorporation of the cargo into the vesicles. Specifically, the increased temperature aids evaporation of the solvent from the cargo, which forces uptake of the cargo by partitioning into the phospholipid bilayer of the vesicle and maintains the hydrophobic cannabinoids in a fluid state.

Thus, according to aspects of the present invention, GMVs and LUVs are provided which offer many advantages. The present GMVs and LUVs are made of lecithin comprising biologically acceptable organic components which are readily available. The GMVs and LUVs are made in an aqueous suspension via a simplified method that docs not involve the formation of emulsions and yields uniform liposome populations. The present vesicles exhibit a high level of structural stability evident by the extended lifespan of the vesicles, e.g. at least about 3 months. In addition, the vesicles are readily prepared in an acidic solution which prevents the growth of pathogenic and spoilage bacteria, thereby providing a product with enhanced anti-microbial properties.

Further, the present GMVs and LUVs can readily take up cargo, and thus, are useful for in vivo delivery of cargo. For example, the present vesicles provided in aqueous solution are useful for the delivery of cargo, including small molecules and macromolecules which may be either hydrophilic or hydrophobic. Thus, the vesicles may be utilized for oral administration, provided for consumption in a liquid, including beverages, e.g. both hot and cold beverages, or combined with other edibles as the liquid component thereof. The vesicles may also be utilised in a therapeutic solution for oral or other forms of administration, e.g. parenteral administration such as by injection, e.g. intravenous, intramuscular or subcutaneous, ocular, nasal, vaginal, anal, etc.

In a further embodiment of the invention, another method of preparing unilamellar vesicles from spontaneously formed giant multi-lamellar lecithin vesicles (GMVs) is provided. The method is advantageous in that homogenization of the GMVs to form smaller vesicles is not required. The method yields vesicles which exhibit good stability and anti-microbial properties with a water activity of less than 0.85.

The method comprises combining spontaneously formed GMVs as previously described (made by combining lecithin with an aqueous buffer) with a low molecular weight polyol (e.g. glycerol or glycols such as ethylene glycol or propylene glycol). The polyol, preferably glycerol, is utilized in an amount of 10-90% by wt, preferably greater than 30% by wt, e.g. 40-90% by wt, to yield vesicles in the range of 50-400 nm, preferably less than 400 nm, 300 nm or 200 nm, such as about 100 nm, or in the range of 50-150 nm. As one of skill in the art will appreciate, the method may yield a population of vesicles that overlap the size range of large and small unilamellar vesicles, e.g. LUV/SUV. The solution may be passed through a rotostator or other similar device to narrow the size distribution of the vesicles, i.e. to yield a more uniform population of vesicles. It is noted that the vesicles may be formed using any combination of lecithin, buffer and polyol. For example, the method may include combining the polyol with lecithin and then adding water (buffer), or by combining the polyol with buffer and then mixing with lecithin. The former method is preferred, i.e. to treat preformed GMVs formed by the combination and admixture of lecithin with buffer, followed by addition thereto of the polyol, e.g. glycerol.

Embodiments of the invention are described by reference to the following specific examples which are not to be construed as limiting.

Example 1. Computer Simulation of the Incorporation of Cannabinoid into 1-Stearoyl-2-Oleyl-Phosphatidylcholine Bilayers Atomic scale molecular mechanics computer simulation of the incorporation of cannabinol in phospholipid bilayers was conducted. For these atomistic simulations, two programs were used, ChemSite Pro version 10.5 (Copyright David Michael, Ph.D) and Molecular Modelling Pro Plus (MMP) version 8.1.40 (Norgwyn Montgomery Software Inc, James A. Quinn, lead programmer). Under ChemSite, the "Build Lipid" function was used which had already formed 1-stearoyl-2-oleyl-phosphatidylcholine (SOPC) bilayers in the database. This constituted the phospholipid bilayer, the main structural component of a phospholipid vesicle. The bilayer was made of 8 SOPC molecules and 32 water molecules (one water layer). The simulation conditions were as follow:

Time step: 1
Total time: 10,000 ps
Bath temperature: 300K
Replay sampling period: 200
Equilibration steps: 200
NBI list refresh period: 20
Cutoff Distance: 7 Å
Initial lipid separation: 7 Å
Periodic Boundaries: 70 Å×15 Å×15 Å
No implicit solvent
Generalized Born solvation model GBV
Heat bath relaxation time (fs): 500

The periodic boundary conditions were critical to this simulation. Without them, the simulations gave erroneous and erratic results and molecules would gradually migrate away from each other. The simulation was carried out as follows. First, the SOPC bilayer was built and its energy minimized within ChemSite using the default Amber minimization. Many characteristics were determined but the focus was on the total energy of the system. Once the first, empty, bilayer structure was minimized, one cannabinol molecule was introduced within the fatty acid chains of the bilayer. The structure was minimized containing the cannabinol molecule, and the minimum energy determined. This process was repeated up to the incorporation of 6 cannabinol molecules within the 8 SOPC molecule bilayer.

Figure 2:
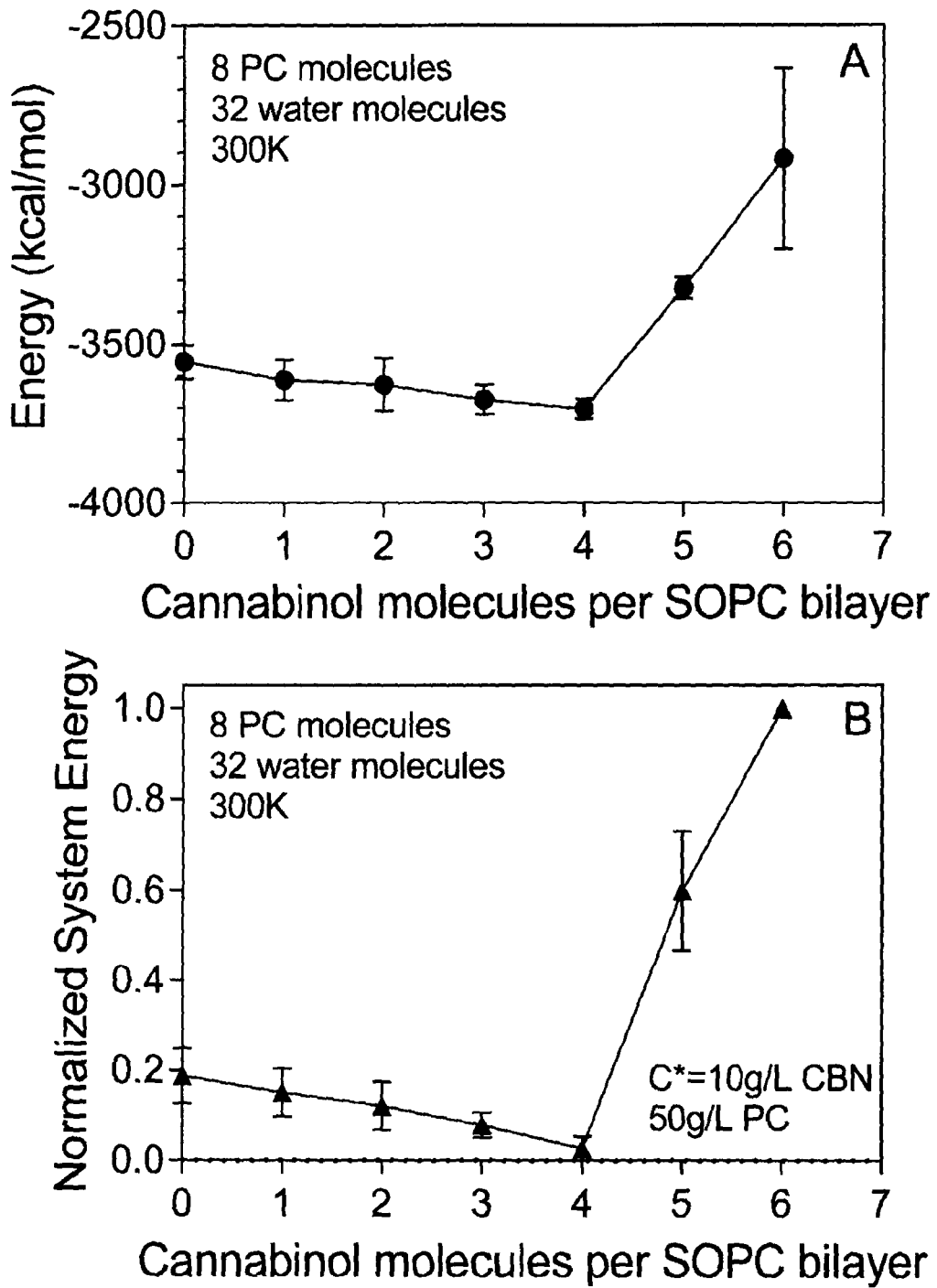
FIG. 2 illustrates atomic scale molecular mechanics simulations of the incorporation of cannabinol into a 1-palmitoyl, 2-oleyl phosphatidylcholine (POPC) phospholipid bilayer in terms of energy (A) and normalized system energy (B)

This simulation was replicated 6 times and means and standard errors reported in FIG. 2 which clearly shows how incorporation of more than 4 cannabinol molecules caused a large increase in the system's energy. The result were reproducible and interpreted as a destabilization of the bilayer if more than 4 cannabinol molecules were present within an 8 phospholipid bilayer corresponding to a 1:2 mol:mol ratio. One very interesting observation is that the incorporation of cannabinol at lower concentrations stabilizes the bilayer slightly as evidenced by a gradual decrease in the system's energy upon incorporation of 4 cannabinol molecules (2:1 mol:mol ratio). FIG. 2 shows the system's energy (FIG. 2A) and the normalized system's energy (FIG. 2B) of the final minimized structure of cannabinol within SOPC bilayers, with water. These studies suggest that cannabinol can be encapsulated within phospholipid vesicles up to a 2:1 mol:mol phospholipid:cannabinol content.

Example 2. Spontaneous, Thermodynamically Stable Giant Multilamellar Vesicles (sGMV)

A multicomponent phospholipid and glycolipid mixture was used for the spontaneous formation of thermodynamically stable vesicles. The soybean lecithin. Phospholipon20 (Lipoid GmbH, Ludwigshafen, Germany) and sunflower lecithin. Sunlec25 (Perimondo, New York, NY, USA) were used. Phosphatidylcholine content is denoted by the number in the lecithin name.

The phospholipid and fatty acid composition of these samples is set out in Table 2. Phospholipid content was provided by the manufacturers. Fatty acid composition was determined as follows. An Agilent 6890-series gas chromatography (Agilent Technologies, Inc., Wilmington, DE, USA) with a 7683-series auto-sampler was used to determine the fatty acid composition of samples. A GC column, BPX70 (SGE Inc. Austin, TX, USA), 60 m×0.22 mm internal diameter with a 0.25 μm film thickness, was used. The oven temperature was programmed to increase from 110° C. to 230° C. (4° C./min) and was maintained at 230° C. for 18 minutes. The injector was set at 250° C. and operated at 20.1 psi with a flow of 17.7 mL/min. High-purity helium, a carrier gas, was flowed at an average velocity of 25 cm/s. A flame ionization detector was set at 255° C. with 450 mL min air and 50 mL/min helium flow rate. The patterns obtained were analyzed using Open LAB software (Agilent Technologies). Fatty acid composition was determined by comparing retention times of the peaks to standards. Values are reported as relative mass ratios.

TABLE 2

Phospholipid and fatty acid composition of the lecithins used in this work.

| Phospholipid | Sunlec25 Sunflower Weight % | Phospholipon20 Soybean Weight % |
|---|---|---|
| Phosphatidylcholine | 25 | 24 |
| Phosphatidylinositol | 29 | 15 |
| Phosphatidylethanolamine | 11 | 22 |
| Phosphatidic Acid | 6 | 7 |
| Minor phospholipids | 4 | 5 |
| Lysophosholipids | 0 | 3 |
| Glycolipids | 15 | 15 |
| Fatty acid | Weight % | Weight % |
| 16:0 | 17.6 | 18.9 |
| 18:0 | 4.1 | 4.0 |
| 18:1 | 11.1 | 9.7 |
| 18:2 | 64.7 | 58.8 |
| 18:3 | n.d | 6.6 |

The fatty acid composition was very similar between the sunflower and soybean lecithins, except for the higher linolenic acid (18:3) content of soybean lecithin. In terms of phospholipid composition, both sunflower and soybean have similar phosphatidylcholine contents, while the phosphatidylethanolamine content of soybean lecithin is about 2× higher than that of sunflower lecithin (22% vs. 11%).

The lecithin powders were dispersed at a 10% (w/w) level in 0.1M citric acid buffer, pH 4 at 40° C. The powder dispersions were gently stirred with an overhead paddle mixer at 200 rpm for 18 hours. All the powder dissolved/dispersed, and the dispersion was analyzed.

First, a standard estimation of the size of the structures created was performed. Particle size distribution determination was carried out via static light scattering using a Mastersizer 2000 (Malvern Instruments Ltd., UK) equipped with a Hydro 2000SM small volume sample dispersion unit. The refractive index of the suspended particles was assumed to be similar to that of phospholipid, and for the continuous phase, deionized water. Refractive index values of 1.42 and 1.33 were used for the dispersed and continuous phases, respectively. Sample was added until an initial obscuration of ~15% was reached. Each measurement was carried out in triplicate, and the average size distribution was reported.

Figure 3:
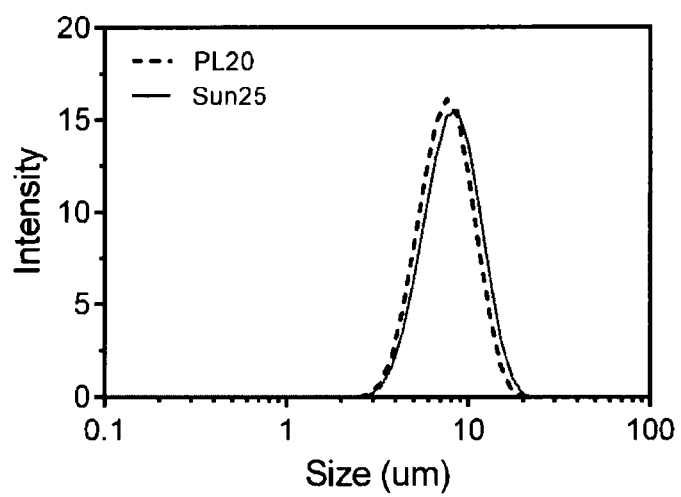
FIG. 3 graphically illustrates the size distribution of spontaneously formed giant phospholipid vesicles from soybean lecithin (PL20) and sunflower lecithin (Sun25) in 0.1M citrate buffer, pH 4.3.

The result of this analysis is presented in FIG. 3. As shown, a relatively narrow size monomodal distribution was obtained without any large aggregates or small structures. This structure formed spontaneously. The size of these phospholipid vesicles was 6.66 (+/−0.07) μm for Phospholipon20 and 7.44 (+/−0.29) μm for Sunlec25. For Phospolipon 20 the span of the distribution was 0.856, while for Sunlec25 it was 0.894.

Phospholipid vesicle structures were then characterized by bright-field microscopy (model DM RXA 2, Leica Microsystems Wetzlar GmbH, Wetzlar, Germany). Dispersions were prepared by 10:1 (v/v) dilution in deionized water, and ~10 μl were pipetted onto a microscope slide prior to applying a glass coverslip. For all images, a 40× objective was used, and the images were captured with a digital camera (Retiga 1300i, QImaging, Surrey, RC, Canada) using the Volocity software package (version 6.2.1; PerkinElmer, Woodbridge, ON, Canada). Images acquired were converted to grayscale and levels adjusted automatically using Adobe Photoshop CS5 (Adobe, San Jose, CA, USA).

Figure 4:
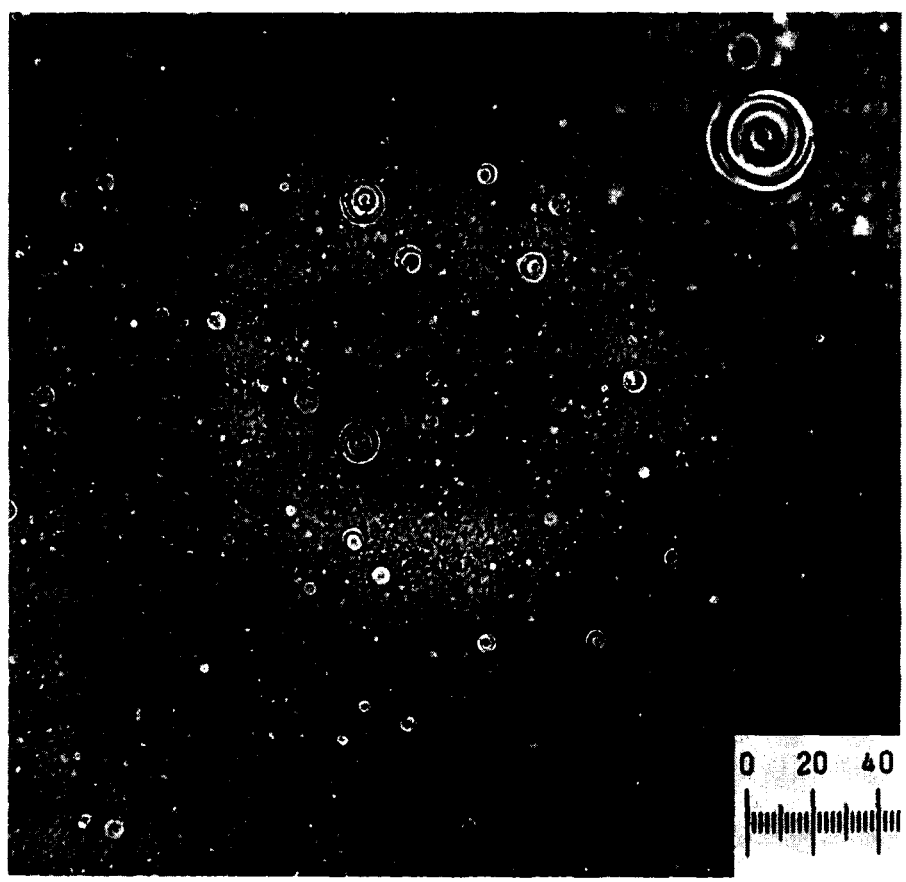
FIG. 4 illustrates a light micrograph of soybean lecithin giant multilamellar vesicles in 0.1M citrate butter, pH 4.3.
Figure 5:
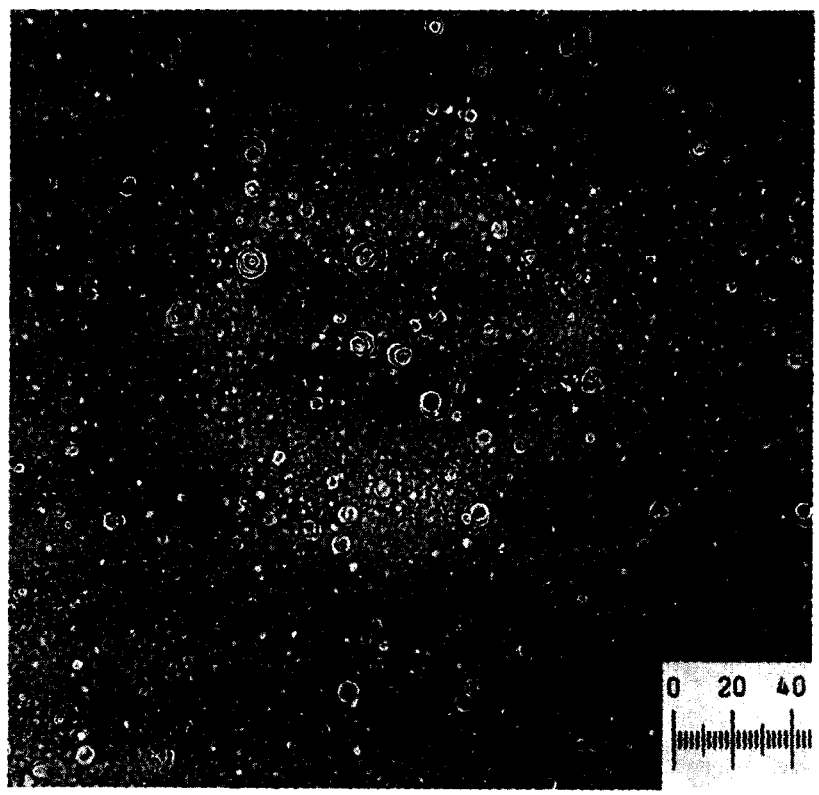
FIG. 5 illustrates a light micrograph of sunflower lecithin giant multilamellar vesicles in 0.1M citrate butter, pH 4.3.

Large vesicles of diameters comparable to that obtained by light scattering were observed, e.g. >6 μm. Moreover, it was also determined that these spontaneously formed vesicles were multilamellar for both soybean (FIG. 4) and sunflower (FIG. 5) lecithin. Thus, the vesicles formed may be classified as spontaneous Giant Multilamellar Vesicles, or sGMVs.

The thermal behavior of the vesicles was also characterized to determine if a phase transition from gel phase to liquid crystalline state existed in the temperature range of interest, namely, just above freezing to 90° C. Thermal behavior was evaluated using a differential scanning calorimeter, the DSC 1 instrument (Mettler-Toledo, Mississauga, ON, Canada). Approximately 10 mg of sample was placed into an aluminum DSC pan and hermetically sealed. Thermograms were obtained using a heating/cooling cycle between 25° C. to 90° C. at a rate of 5° C./min, with a 3 min isothermal period between the dynamic stages. Curves were evaluated using the Star Software (Mettler-Toledo) provided with the DSC unit.

Figure 6:
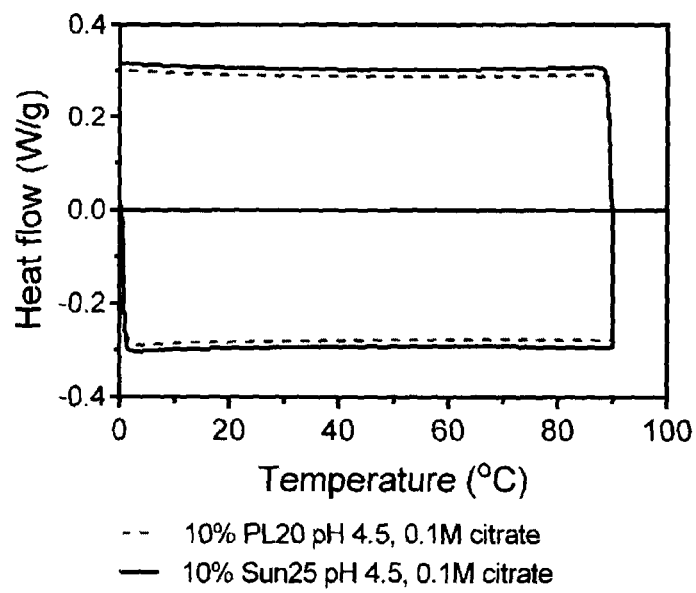
FIG. 6 illustrates differential scanning calorimetric scans of the spontaneous giant multilamellar vesicle, both heating (endothermic, negative heat flows) and cooling (exothermic, positive heat flows)

Results from this analysis are shown in FIG. 6. Negative (endothermic) heat flows correspond to heating while positive (exothermic) heat flows correspond to cooling. No thermal transition was evident at all. This is important since vesicles manufacture usually takes place in the liquid crystalline state. Moreover, vesicles are generally more stable in their liquid crystalline state, rather than in their gel state. This is ensured by using highly unsaturated phospholipids, There also did not seem to be any stability issues associated with a phase change according to the DSC analysis.

Figure 7:
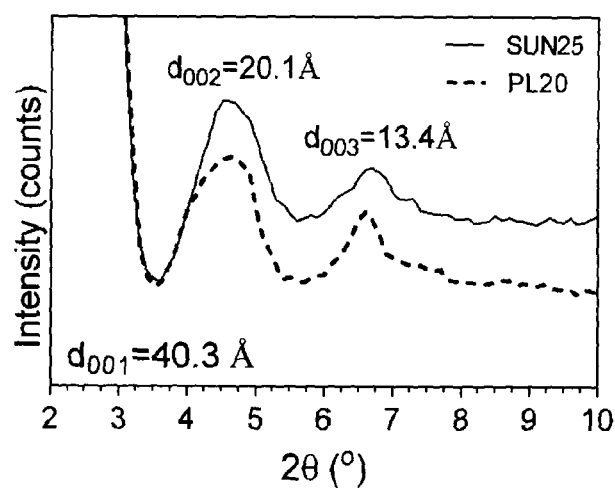
FIG. 7 illustrates powder X-ray diffraction patterns for spontaneously formed giant multilamellar vesicles prepared using soybean and sunflower lecithin.

An important structural aspect of vesicles is that they are bilayers in a lamellar phase. This so-called mesomorphic or polymorphic state/phase of self-assembly can be determined using small-angle powder X-ray diffraction (SAXS). X-ray scattering experiments were carried out using a Rigaku Multiflex Powder X-ray diffraction spectrometer (Rigaku, Tokyo, Japan). The copper X-ray tube (wavelength of 1.54 Å) was operated at 40 kV and 44 mA. The measurement scan rate was set at 0.1°/minute in the range 2θ=1°-15° at 22° C. Peak positions were determined using MDI Jade 9 (MDI, Livermore, CA, USA) software. The SAXS pattern obtained for the spontaneous GMVs is shown in FIG. 7. The relative spacing of the diffraction peaks was 1:2:3 in terms of the center position of the peaks, which is indicative of the existence of a lamellar phase (Zetzl et al. 2009).

Thus, these experiments confirm the spontaneous formation of giant multilamellar vesicles using commercial dry and deoiled lecithin.

Example 3. Preparation of LUVs from GMVs Using a Rotor-Stator

The thermal and shear stability of the spontaneous GMVs (sGMVs) was compared to that of 1110 nm large unilamellar vesicles (LUV) prepared using a rotor-stator. The Magic Lab machine of IKA (IKAWorks, Inc., Wilmington, NC, USA) was used to prepare the LUVs. The DR Dispatch reactor unit with 3 toolings in series, two very fine toolings with 3 shear zones per tooling, and one "centrifugal pump" tooling, was used. The sample has to flow through a narrow gap in between a stationary plate with holes (stator) and a rotating plate with holes (rotor). Fluid velocities can be very high in the openings and 26,000 rpm rotational speeds are possible. This machine functions under the same principle as an "Utra-Turrax" hand-held rotor-stator. As a matter of fact, one can use an "Ultra-Turrax" tooling with this machine if required.

Figure 8:
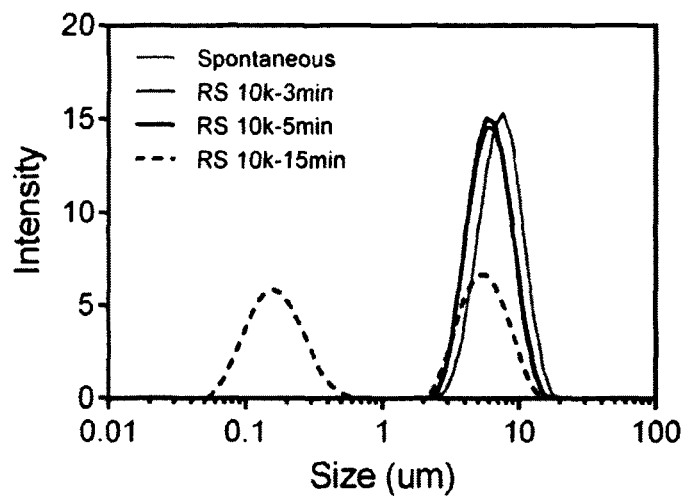
FIG. 8 graphically illustrates the size distribution of soy lecithin spontaneous giant multilamellar vesicles sheared in a rotor-stator for different periods of time.

First, the sensitivity of the spontaneous vesicles was monitored as a function of shear (FIG. 8). About 100 ml of soy lecithin sGMVs were sheared for 3, 5 and 15 minutes in the IKA rotor-stator mixing device at 10,000 rpm. My using this volume, the recirculation of the fluid was fast and the 100 mL were effectively continuously passed through the three toolings. Due to shear heating, it is important to keep the temperature of the sample below 80° C., which was achieved by flowing cold water through the rotor-stator assembly. The soy lecithin sGMV could withstand up to 5 minutes of shear at 10,000 rpm. Surprisingly, after 15 minutes, a large proportion of the 6.5 μm sGMVs had been reduced in size to ~160 nm. Intermediate sizes (between 6.5 μm and 160 nm) were not observed.

Figure 9:
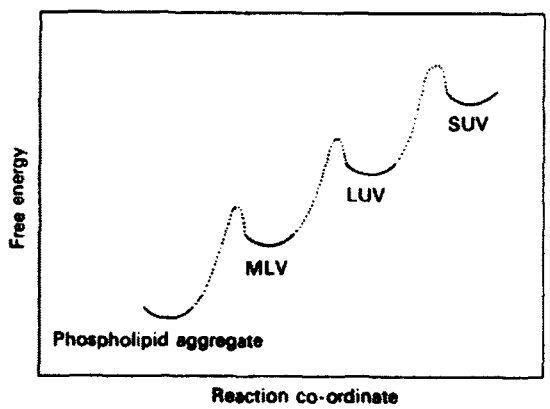
FIG. 9 illustrates the free energy reaction coordinate depicting the increasingly higher energy states of smaller vesicles.

This suggests that the spontaneous GMVs were occupying a well-defined quantized thermodynamic state. Energy input eventually results in taking the system out of equilibrium into a higher energy state, namely, the large unilamellar vesicle state shown in a free energy reaction coordinated diagram (FIG. 9). Small unilamellar vesicles (SUVs) could not be achieved with a rotor-stator regardless of the time or rpm used. For this purpose, a higher energy input would be required, such as the one achievable using a microfluidizer, or other technique.

Figure 10:
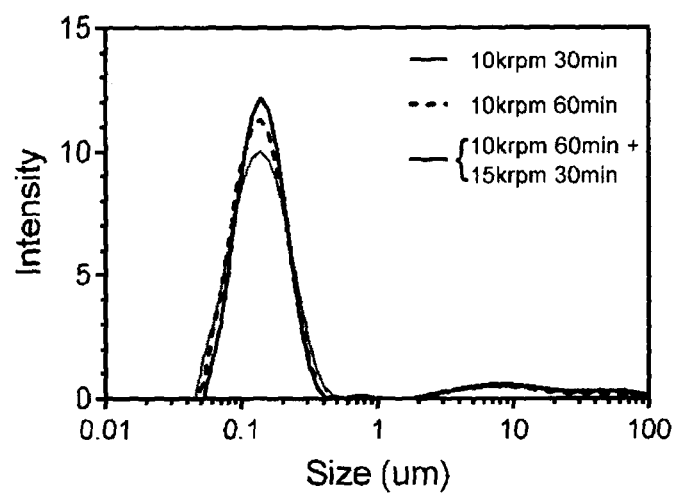
FIG. 10 graphically illustrates size distribution of sunflower lecithin large unilamellar vesicles sheared for different times at different shear rates.

Size reduction experiments were also conducted on 10% sunflower lecithin, Sunlec25, in 0.1M citrate buffer, pH 4.5. As shown in FIG. 10, 30 min of shearing in a rotor-stator at 10,000 RPM was sufficient for size reduction of sunflower lecithin into the ~100 nm range. Further shearing for 1 hour did not change the distribution.

Figure 11:
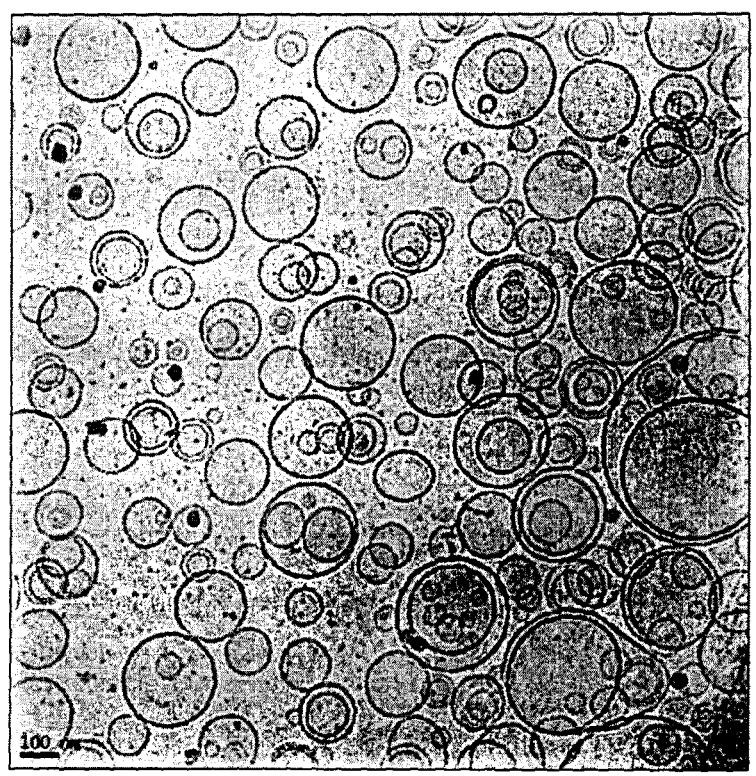
FIG. 11 illustrates cryogenic transmission electron microscopy of soybean lecithin large unilamellar vesicles.

The existence of LUVs was confirmed by cryogenic transmission electron microscopy. In preparation for imaging by cryo-TEM, 5 μl of sample were transferred onto a Quantifoil multi-hole grid which had been glow discharged. The suspension was then thinned by blotting with filter paper, and plunged into liquid ethane which was held close to liquid nitrogen temperature. The grid was stored in liquid nitrogen prior to being loaded into a pre-cooled holder which is inserted into a Tecnai TEM (Thermo Scientific, USA). Samples were viewed at −175° C. and 200 kV, and images were recorded using the Gatan 4K camera and the Gatan Digital Micrograph software (Gatan Inc., Roper Technologies, USA). FIG. 11 shows soy lecithin LUVs created using the rotosator. The single bilayer surrounding the vesicles and the average size of these can be appreciated from this micrograph. sGMVs were converted into LUVs using a rotor-stator. This is the first time such size reduction has been reported using a rotor-stator. Rotor-stators are used to make "pre-emulsions" and have never been listed as a viable method to make unilamellar vesicles. The average surface weighted diameters (D3,2) and standard deviations of the lecithin LUVs were determined by static light scattering measurements using a Mastersizer to be 115+/−3.12 nm for soybean PL20 and 116+/−1.41 nm for sunflower Sunlec25 lecithin.

Figure 12:
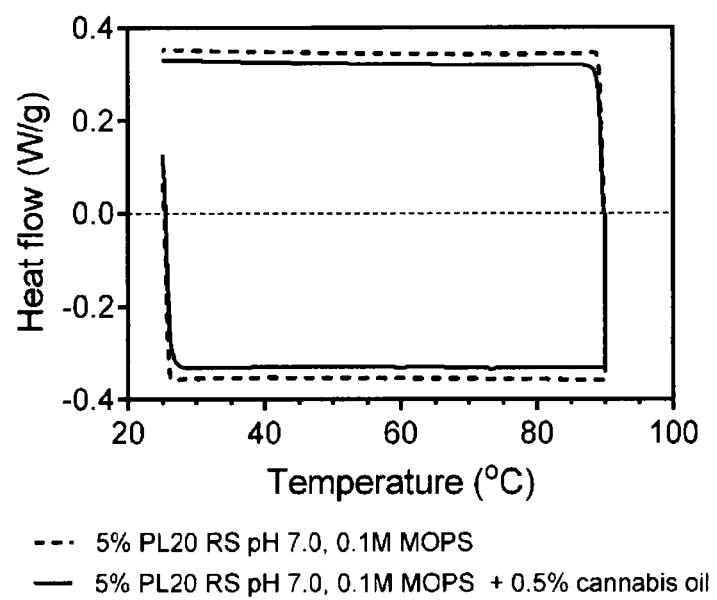
FIG. 12 are differential scanning calorimetric scans of soybean lecithin large unilamellar vesicles in 0.1M MOPS buffer, pit 7.2, both in heating (negative heat flows) and cooling (positive heat flows) modes.

The melting and cooling of the vesicles monitored by differential scanning calorimetry did not reveal any thermal phase transitions between freezing and 90° C. This is not surprising since the majority of the fatty acids of these lecithins are linoleic and linolenic acids, which have very low melting points (FIG. 12).

Example 5. Thermal Stability of sGMVs and LUVs

To use the present vesicles in foods/drinks, they would have to be pasteurized or sterilized. Thus, the thermal stability of the vesicles is important. To determine their thermal stability, two sets of experiments were conducted, one at 90° C. for 105 min and the second one at 60° C. for 160 hrs. Scaled glass containers of both vesicles preparations were placed in ovens at the two temperatures and following heating, the diameter of the vesicles were determined by static light scattering using a Mastersizer 2000.

Figure 13:
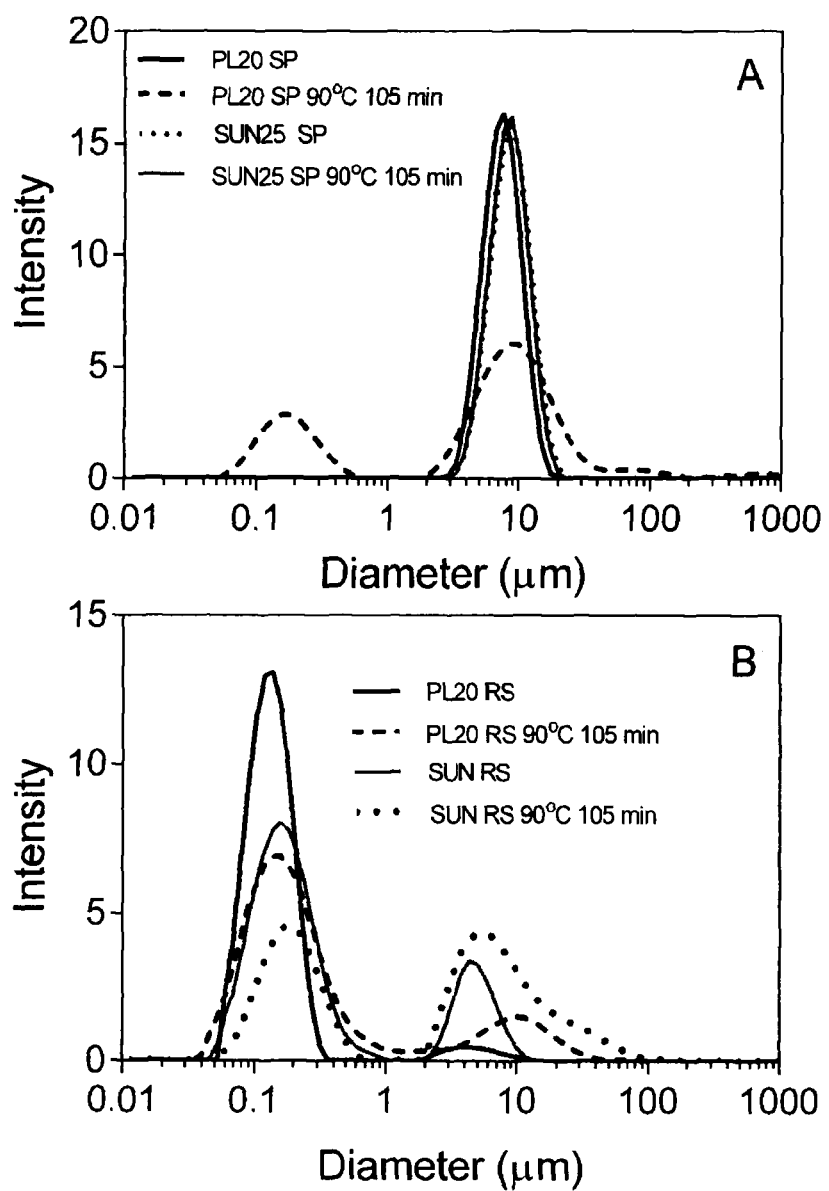
FIG. 13 graphically illustrates size distributions for soy and sunflower lecithin-derived spontaneous giant multilamellar vesicles (A) and large unilamellar vesicles (B) in 0.1M citrate buffer, pH 4.3, exposed to 90° C. for 105 min.

FIG. 13A clearly demonstrates how the average diameter of the sunflower lecithin sGMVs does not change during 1 hour and 45 minutes exposure to near boiling temperatures. However, exposure to high temperature caused a widening of the size distribution of soy lecithin vesicles and also resulted in the appearance of ~160 nm structures. It was not clear whether these were LUVs or some kind of micelle. Regardless, the soy lecithin showed a lower thermal stability than the sunflower lecithin, winch may be a due to differences in molecular composition, namely higher PE contents and higher levels of the highly unsaturated linolenic acid.

FIG. 13B, on the other hand, shows the behavior of the corresponding LUV versions of these vesicles. For these experiments, samples were sheared in the IKA Magic Lab rotor-stator as described above for 1 min at 10,000 RPM and 4 min at 25,000 RPM at 30° C. Two interesting aspects of these systems were revealed. First, where the rotor-stator conditions were sufficient to yield a narrow size distribution for the PL20 soybean lecithin, they were not sufficient to fully convert all sGMVs into LUVs for Sunlec25 sunflower lecithin. This may be due to the soy lecithin sGMVs being less stable than the sunflower lecithin sGMVs, which resisted the transformation into LUVs. Upon exposure of these LUV preparations to the high heat conditions, both systems destabilized as evidenced by the appearance of a population of larger vesicles that may result from the combined effect of flocculation and coalescence. What is remarkable, though, is that the spontaneous sunflower GMVs were completely stable (FIG. 13A), where the corresponding sunflower LUVs were clearly not as stable (FIG. 13B). This provides support for the thermodynamic stability of sGMVs vs. the kinetic stability of LUVs.

The decreased stability of soy lecithin over sunflower lecithin could be due to the preference of certain polar lipids for specific mesomorphic phases. Tillock discussed this at length and a table (Table 3) from his 1986 paper is shown below (Tillock, 1986). One can immediately notice that phosphatidylethanolamine in isolation prefers to form Hex-II phases.

TABLE 3

Polymorphic phase preferences of liquid crystalline unsaturated lipids.
POLYMORPHIC PHASE PREFERENCES OF LIQUID
CRYSTALLINE UNSATURATED LIPIDS

| Lipid | Phase preferences Physiological conditions | Other conditions |
|---|---|---|
| Phosphatidylcholine | L | $H_{II}$ low hydration and high temp |
| Sphingomyelin | L | — |
| Phosphatidylethanolamine | $H_{II}$ | L, pH ≥ 8.5 low temp |
| Phosphatidylserine | L | $H_{II}$, pH ≤ 3.5 |
| Phosphatidylglycerol | L | $H_{II}$, high temp, high salt conc. |
| Phosphatidylinositol | L | |
| Cardiolipin | L | $H_{II}$, divalent cations, pH ≤ 3, high salt |

TABLE 3-continued

Polymorphic phase preferences of liquid crystalline unsaturated lipids.
POLYMORPHIC PHASE PREFERENCES OF LIQUID
CRYSTALLINE UNSATURATED LIPIDS

| | Phase preferences | |
|---|---|---|
| Lipid | Physiological conditions | Other conditions |
| Phosphatidic acid | L | $H_{II}$, divalent cations, pH ≤ 3.5, high salt |
| Monoglucosyldiglyceride | $H_{II}$ | |
| Diglucosyldiglyceride | L | |
| Monogalactosyldiglyceride | $H_{II}$ | |
| Digalactosyldiglyceride | L | |
| Cerebroside | L | |
| Cerebroside sulfate | L | |
| Ganglioside | M | |
| Lysophosphatidylcholine | M | |
| Cholesterol | | Induces $H_{II}$ phase in mixed lipid systems |
| Unsaturated fatty acids | | Induce $H_{II}$ phase |

Note:
L, Lamellar; $H_{II}$, hexagonal; M, micellar.

Figure 14:
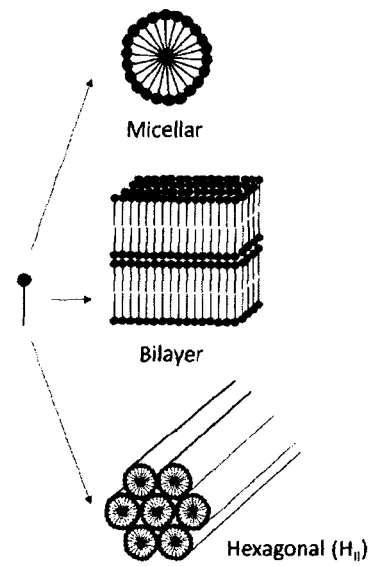
FIG. 14 illustrates polymorphic or mesomorphic preference of polar lipids and their associated overall molecular shape.

FIG. 14 illustrates mesomorphic structures in relationship to their overall molecular "shape" (Tillock, 1986; Cullis et al., 1986).

As set out in Table 2, soybean lecithin contains twice the amount of phosphatidylethanolamine (PE) than sunflower lecithin. This larger amount of PE could be responsible for the polymorphic/mesomorphic instability of soybean lecithin at high temperatures. The PC/PE ratio in soybean lecithin is 1, while the same ratio in sunflower lecithin it is 1.8. The relative amounts of PC vs. PE is much higher in sunflower lecithin due to a much lower PE content. A high PE content is associated with a greater tendency to form Hex-II structures, which may lead to vesicles destabilization. Soy lecithin is also more unsaturated than sunflower lecithin, which also induces lamellar-to-hexagonal II phase transformations. In general, increased unsaturation, increased temperature, decreases in headgroup size, decreases in headgroup ionization and decreases in water content all enhance the destabilization of lamellar phases into hexagonal-II phases, which leads to the formation of cylindrical micelles and vesicles breakdown.

Figure 15:
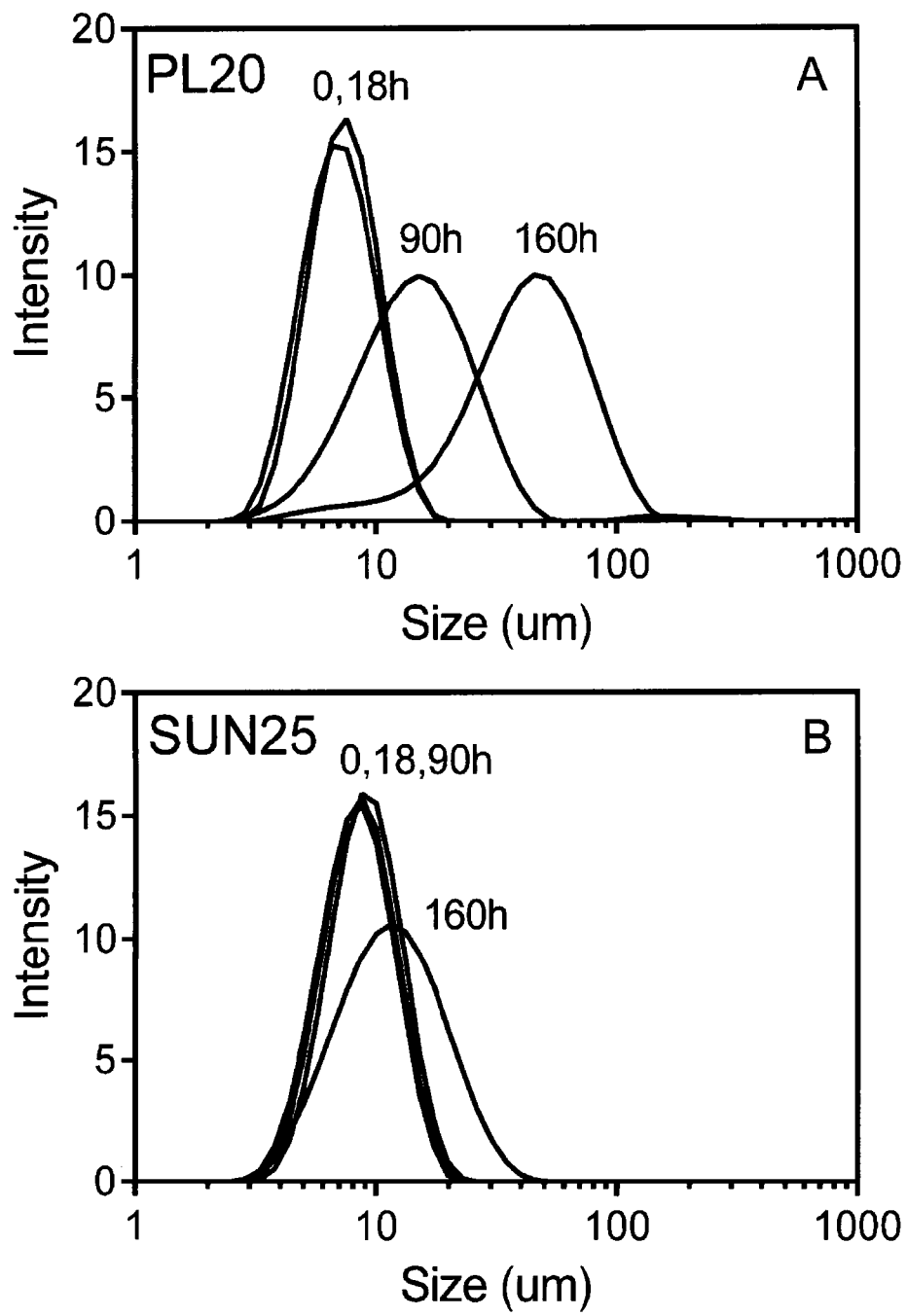
FIG. 15 graphically illustrates size distributions of (A) soybean and (B) sunflower spontaneous giant multilamellar vesicles heated at 60° C. for up to 7 days.
Figure 16:
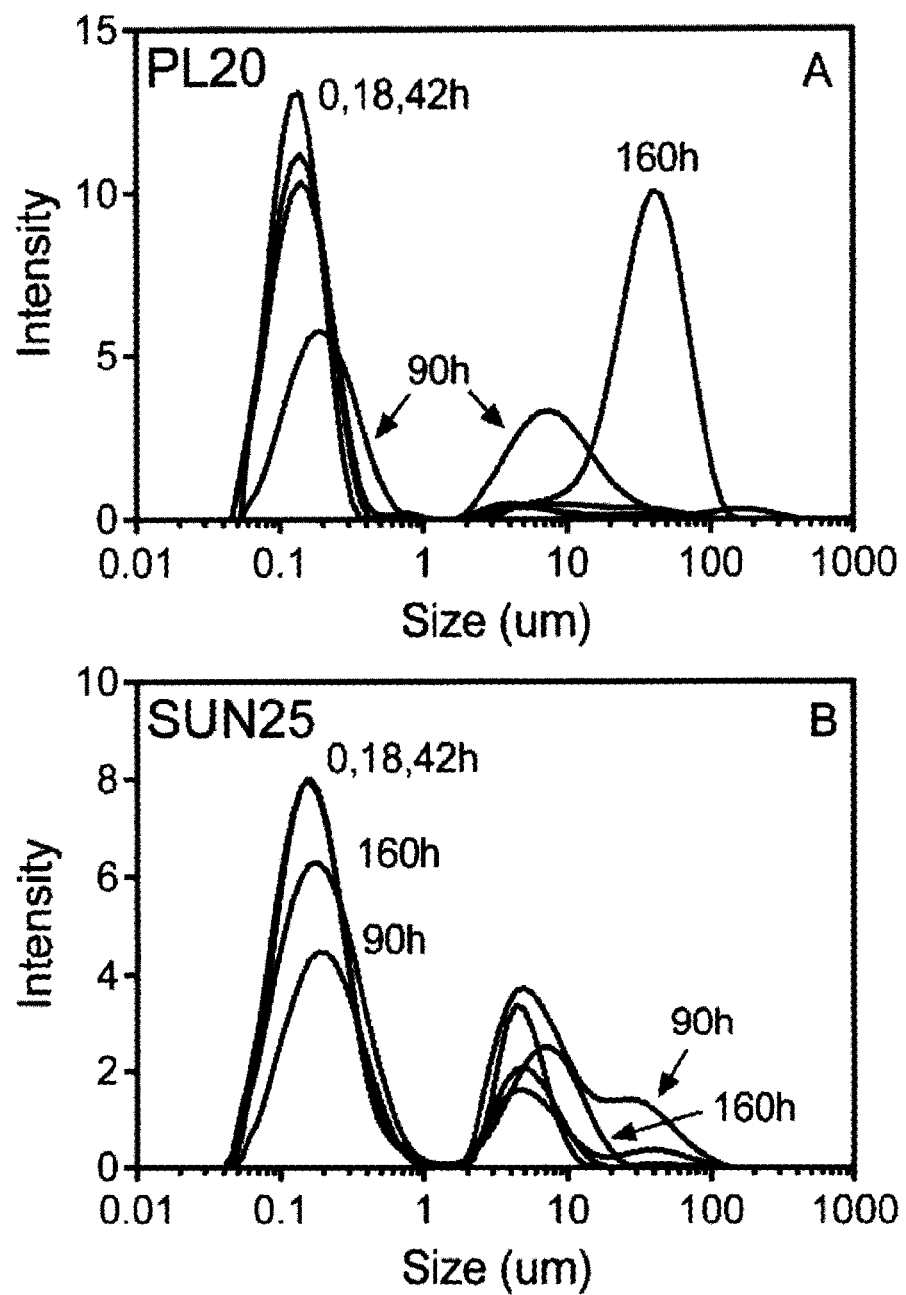
FIG. 16 graphically illustrates size distributions of (A) soybean and (B) sunflower large unilamellar vesicles heated at 60° C. for up to 7 days.
Figure 17:
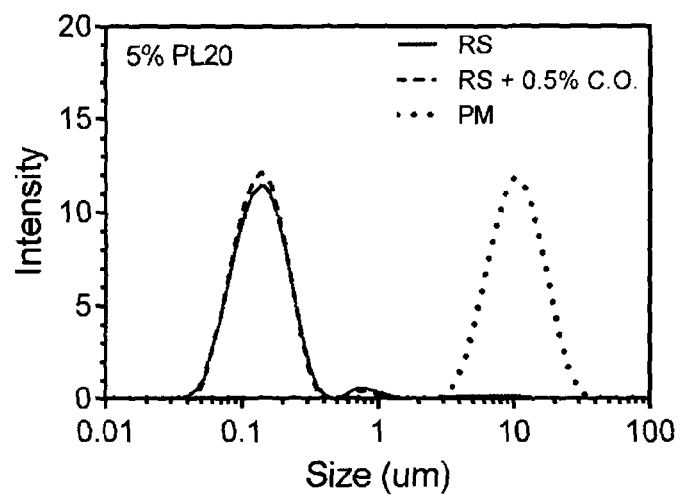
FIG. 17 graphically illustrates size distribution of soy lecithin large unilamellar vesicles containing cannabis oil.

The heat stability experiments were repeated at 60° C. FIG. 15 shows the behavior of the sGMVs while FIG. 17 show's the behavior of the LUVs. Again, sunflower sGMVs (FIG. 15A) were more stable than soybean sGMVs (FIG. 15B). Destabilization occurred after 90 h for soybean lecithin vs. 160 hrs for sunflower lecithin. For the LUVs, similar results were obtained, where soybean lecithin vesicles (FIG. 16A) destabilized before and to a greater extent than sunflower lecithin vesicles (FIG. 16B). These results suggest that higher amounts of monounsaturated fatty acids, such as oleic acid, provides increased oxidative stability, a greater tendency for vesicles to remain in the lamellar phase, as well as remaining in the liquid crystalline state (vs. gel state) over the temperature range 0-90° C.

Example 6. Manufacture, Characterization and Stability of Vesicles Containing Cannabis Oil Cannabis oil was then encapsulated within the phospholipid bilayers of both sGMVs and LUVs. Cannabis oil was first dissolved in 95% ethanol (0.5 g/ml) and then added slowly (1 drop every 0.3 seconds) into a 10% lecithin suspension at 60° C. This is an antisolvent technique in which the cannabis oil became insoluble in the new solvent medium and partitioned into the vesicles membranes since they are the only hydrophobic medium in the system. Cannabis oil in ethanol can be added to phospholipid at different stages, e.g. to a suspension of spontaneous GMVs, LUVs, or during the actual size reduction step in the rotor-stator.

Figure 18:
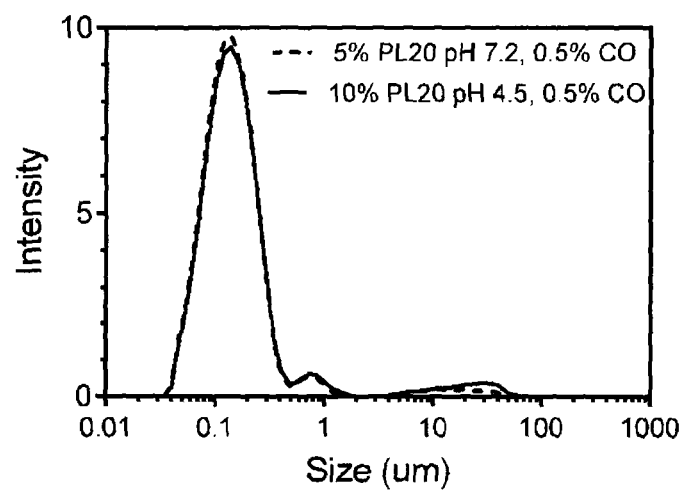
FIG. 18 graphically illustrates the size distribution of soy lecithin large unilamellar vesicles containing cannabis oil in either 0.1M MOPS pH 7.2 and 0.1M citrate pH 4.3.

The first experiment was earned out with soybean lecithin. A 5% (w/w) suspension of spontaneous GMVs was prepared at 60° C. using u puddle mixer. Specifically, a 10 g amount of Phospholipon 20 was added to a solution of 0.1M MOPS (3-(N-morpholino)propanesulfonic acid), pH 7.2 buffer. This mixture was paddle mixed at 300 RPM for 1 hour. The lecithin was fully dissolved in this period. A 100 mL aliquot of this sample was then transferred to the IKA Magic Lab machine. The temperature was maintained between 60 and 70° C. by water recirculation. Temperatures above 80° C. proved deleterious to LUV manufacture and phase separation sometimes occurred. The sample was then sheared at 20,000 RPM for 30 minutes. One milliliter of the 0.5 g/ml cannabis oil in ethanol solution was slowly dripped into the vortex of the IKA Magic Lab rotor-stator while the machine was running. The results from this experiment are shown in FIG. 17. The figure illustrates the step-function like decrease in size from sGMVs to LUVs and the fact that incorporation of cannabinoids did not change this distribution. The stability of these vesicles was monitored for over two months and the size distribution did not change (FIG. 18). Moreover, vesicles formed using 10% soy lecithin in 0.1M sodium citrate pH 4.5 also did not have an impact on physical stability of the LUVs (FIG. 18). However, the pH must be greater than the pK of the phosphate group of the phospholipid to avoid its protonation which would adversely affect liposome stability. Conducting the cannabis incorporation at pH 4.5 advantageously represents a hurdle or barrier to microbial growth and thus constitutes a better system for the commercial production of encapsulated cannabis oil. In addition, since the procedure was carried out at 60-70° C. for over half an hour, the material has effectively also been pasteurized.

Encapsulation, as above, was conducted using 50% phosphatidylcholine lecithin, mainly Sunlipon50. Addition of cannabis oil to 10% sunflower lecithin LUVs in 0.1M citrate buffer pH 4.5 resulted in coagulation and separation of a brown precipitate at 0.5% cannabis oil levels. Thus, lecithin of less than 50% phosphatidylcholine is preferable.

Encapsulation studies of cannabis oil in both sGMVs and LUVs were then conducted using soybean and sunflower lecithin. 10% w/w liposomal suspensions were prepared as described above in 0.1M sodium citrate pH 4.5 comprising entrapped/encapsulated cannabis oil dissolved in 95% ethanol. These samples had a final added concentration of 5, 10, 15 and 20 mg/mL cannabis oil for 100 mg/mL of lecithin.

After encapsulation, samples were centrifuged at 4000 rpm for 10 minutes at room temperature in order to remove any cannabinoids not hound specifically to the vesicles. An aliquot of the supernatant of the labelled liposomal preparations was then extracted using the Bligh and Dyer method (Canadian Journal of Biochemistry and Physiology, 1959, 37: 911-917). The lower chloroform layer of the extract contained the lipid-soluble components, namely the cannabinoids. The composition of this extract was determined using gas-liquid chromatography. An Agilent 6890-series gas chromatograph (Agilent Technologies, Inc., Wilmington, DK, USA) with a 7683-series auto-sampler was used to determine the amount of cannabinoid in the samples. A 15 m×0.25 mm internal diameter fused silica column with a 0.20 μm DB5 film thickness was used (Agilent Inc., USA). The oven temperature was maintained at 80° C. for 5 minutes and then programmed to increase from 80 to 300° C. at 12° C./min. The injector temperature was set at 250° C., and was operated at 19.2 psi with a hydrogen flow rate of 85 mL/min. Split ratio was set at 10:1. Helium, the carrier gas, flowed at an average velocity of 25 cm/s. A flame ionization detector was set at 350° C. with 450 mi/min air and 50 mL/min helium flowing. The separated peaks were analyzed using Open LAB software (Agilent Technologies). The amount of cannabinoid was determined by comparing retention times of the peaks to an internal standard.

Figure 19:
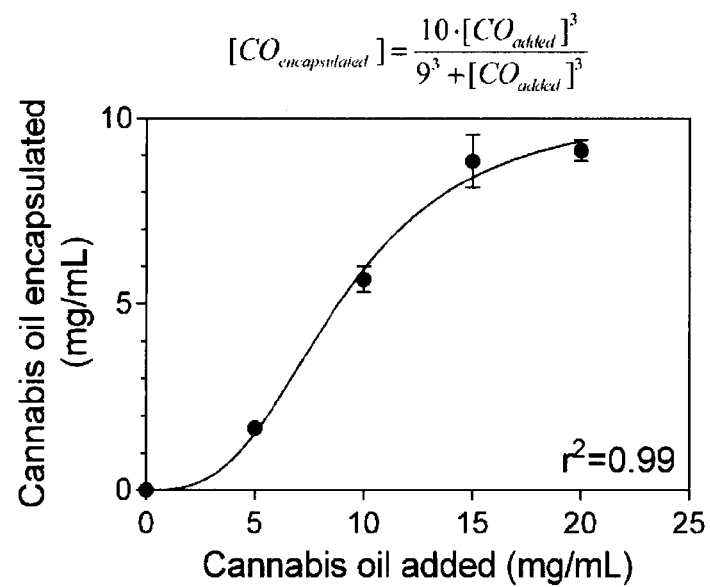
FIG. 19 graphically illustrates encapsulation efficiency of cannabis oil in LUVs prepared from 10% sunflower lecithin in 0.1M citrate buffer, pH 4.3. The fit shown is for specific cooperative binding reaching saturation.

Results are shown in FIG. 19. The results demonstrate that the ~100 nm LUVs do not inherently have the capacity to incorporate high levels of cannabis oil within their structure. This is possibly due to the higher curvature of within these 'smaller' vesicles, which would put strain on the bilayer if cannabinoids become incorporated at high levels. A specific and cooperative saturation binding model fit the data, which suggests that the cannabinoids were partitioning into the membranes and binding specifically to the phospholipids in the bilayer. The cooperative effect could indicate that the hi layer needs to rearrange to welcome cannabinoids within its structure. Once the membrane is "primed", it can then uptake more cannabinoid. The model also indicates a maximal loading capacity of 10 mg/mL for this 10% sunflower lecithin composition structured as LUVs of approximately 100 nm in diameter. This constitutes about 50% encapsulation efficiency for the LUVs.

Figure 20:
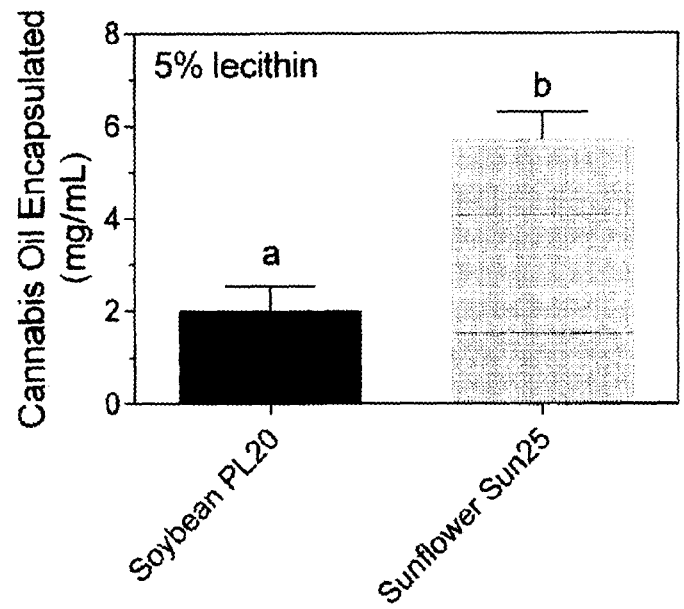
FIG. 20 graphically illustrates encapsulation of cannabis oil in LUVs prepared from soybean and sunflower lecithin in 0.1M citrate buffer, pH 4.3.

FIG. 20 illustrates that sunflower lecithin is much more efficient in encapsulating cannabis nil than soybean lecithin. Encapsulation efficiency of cannabinoid in sunflower lecithin was ~50-60%, while the soybean lecithin LUVs exhibited a ~3× lower encapsulation efficiency than the sunflower lecithin. These results also suggest that incorporation of cannabis oil into sunflower lecithin LUVs is more efficient than in soybean lecithin LUVs. The 50 mg of lecithin present in 1 mL of suspension can easily trap 5-6 mg of cannabis oil. This 1:10 w/w (cannabis oil to lecithin) ratio translates to a 1:4 mol/mol ratio.

Figure 21:
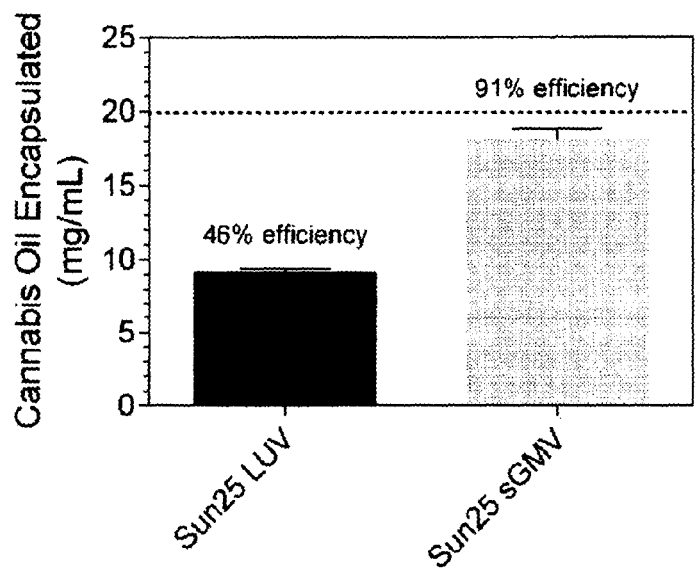
FIG. 21 graphically illustrates encapsulation of cannabis oil in LUVs and sGMVs prepared using 10% sunflower lecithin. Cannabis oil was added at 20 mg/mL levels to the dispersion in 0.1M citrate buffer at pH 4.3.

The experiment was repeated comparing LUVs with sGMVs. The results are shown in FIG. 21. Encapsulation efficiency of the sGMVs prepared form 10% sunflower lecithin was almost 90%, while in contrast the efficiency for LUVs prepared using the same 10% sunflower lecithin was about half of that. Thus, for the sGMVs containing 100 mg of lecithin per ml, 18.1 mg of cannabis oil could be encapsulated per ml, which translates to 1:2.3 mol/mol cannabis oil:lecithin ratio.

These results indicate that it is possible to prepare 10% sGMV phospholipid dispersions containing close to 20 mg/mL cannabis oil, without any loss of the valuable product. The data further indicates that it is also possible to make LUV phospholipid dispersions with 50% encapsulation efficiency. Obviously the smaller vesicles would yield a more translucent sample upon dilution, while with sGMV higher loadings more turbid solutions would be obtained.

Example 7. Antioxidant Activity of Cannabis Oil in Vesicles Combined with Antioxidants One of the greatest problems with the use of cannabis oil is the oxidation of the active component, tetrahydrocannabinol (THC), to cannabinol (CBN); however, it is noted that THC and CBN should have antioxidant activity due to the phenolic ring(s) they contain.

To investigate this, accelerated oxidation tests of cannabis oil in the labile soybean oil with and without additional antioxidants were conducted. The Rancimat (Metrohm MG, Herisau, Switzerland) test was used for this purpose as follows. 2 g of oil were placed in a narrow glass flask, heated to 110° C. and air was bubbled through the oil at 20 ml/min. This caused accelerated oxidation. As the liquid oxidized, volatile secondary oxidation products were volatilized and bubbled into room temperature water. This caused them to dissolve in the water, which results in an increase in its electrical conductivity. The conductivity is measured continuously using a standard electrode. It is noted that the oxidation flasks were cleaned with an industrial degreaser since results are significantly affected by any contamination within the flasks. Results are shown in Table 4.

TABLE 4

Induction times of oxidation determined using the Rancimat method at 110° C.

| Sample | Rancimat Induction time (hr) | Induction time extension (hr) |
| --- | --- | --- |
| Soybean Oil (SBO) | 8.2, 8.3, 7.8[a] | 0 |
| SBO + 0.1% water | 5.8 | −2 |
| SBO + 0.01% TBHQ | 15.3[b] | 7.1 |
| SBO + 0.02% TBHQ | 22.5 | 14.3 |
| SBO + 0.04% TBHQ | 36.7 | 28.5 |
| SBO + 0.5% SUN25 | 11.9 | 4.1 |
| SBO + 0.5% SUN25 + 0.01% TBHQ | 27.6 | 19.8 |
| SBO + 0.5% PL20 | 19.8 | 12 |
| SBO + 0.5% PL20 + 0.01% TBHQ | 28.4 | 20.6 |
| SBO + 2.5 mg/g cannabis oil | 8.5 | 0.7 |
| SBO + 4.8 mg/g cannabis oil | 10.1 | 2.3 |
| SBO + 8.0 mg/g cannabis oil | 11.3 | 3.5 |
| SBO + 4.8 mg/g cannabis oil + 0.01% TBHQ | 15.7 | 7.9 |
| SBO + 4.8 mg/g cannabis oil + 0.5% SUN25 | 17.4 | 9.6 |
| SBO + 4.8 mg/g cannabis oil + 0.5% SUN25 + 0.01% TBHQ | 28.8 | 21 |
| SBO + 4.8 mg/g cannabis oil + 0.5% PL20 | 25.2 | 17 |
| SBO + 4.8 mg/g cannabis oil + 0.5% PL20 + 0.01% TBHQ | 32.1 | 23.9 |

[a]Different sources of soybean oil displayed different sensitivities towards oxidation. The soybean oil used for these experiment had an induction time of 7.8 hours.
[b]These three experiments of THBQ addition to SBO were carried out with soybean oil with an induction time of 8.2 hours As shown in Table 4, the induction time for Rancimat oxidation of soybean oil was ~8 hours. This value was highly reproducible across three different types of soybean oil. Interestingly, addition of just 0.1% water decreases the oxidative stability of the oil significantly by two hours, probably due to hydrolysis of the triglycerides to fatty acids, which then can volatilize and/or oxidize. As a positive control, increasing levels of the most powerful synthetic phenolic antioxidant, TBHQ (tert-butylhydroquinone). The usual usage level of TBHQ is 0.01% (w/w), which is equivalent to 100 ppm, and this provides a shelf life to most vegetable oils of one year at ~25° C. For every 100 ppm TBHQ added to the oils, the induction time of oxidation increased by 7.1-7.2 hours, in a linear fashion ($t_i=8.12+0.07154$[ppm TBHQ], $r^2=0.99$).

It was then determined whether or not cannabis oil had antioxidant activity. Addition of cannabis oil to soybean oil at a level of 8 mg/g of oil displayed antioxidant behavior and increased the induction time of oxidation of the soybean oil by 3.5 hours at 110° C. To clarify, this means that cannabis oil will oxidize preferentially over soybean oil, thus protecting soybean oil from oxidation. Addition of 0.01%

TBHQ to soybean oil containing 4.8 mg/g cannabis oil increased the induction time of oxidation from 7.8 hours to 15.7 hours. This is consistent with a simple linear addition of the respective induction times of oxidation for the different components. No interaction between the TBHQ and the cannabinoids was observed, and the cannabis oil did not oxidize during this period since an induction time of 18 hours was not attained.

The antioxidant activity of the deoiled and dried lecithins (soybean and sunflower lecithin) was determined. These were added to soybean oil. Unexpectedly, both soybean and sunflower lecithins displayed strong antioxidant potential at 0.5% addition levels, extending the induction time of oxidation from 7.8 hours to 11.9 hours for Sunlec25 and to 19.8 hours for PL20. Please note that at 5 mg/g addition, the concentration is 50 times higher than TBHQ, but in the range of cannabis oil. Since lecithin is not usually considered an antioxidant, this finding was surprising. It also means that encapsulation of cannabis oil within lecithin could protect the active components in cannabis oil, particularly THC against oxidation.

The effects of 0.01% TBHQ addition to soybean oil with 0.5% lecithin was then determined. Again, surprisingly, this combination was found to increase induction times from 11.9 to 27.6 hours for sunflower lecithin and from 19.8 to 28.4 hours for soybean lecithin. Addition of TBHQ to soybean oil alone increased the induction time by 7.1 hours only, but in combination with lecithin, induction time was increased an additional 15.7 hours and 17.4 hours for sunflower and soybean lecithin, respectively. This massive increase in induction time can only be interpreted as a strong synergistic effect between lecithin and phenolic antioxidants such as TBHQ.

Addition of both lecithin and cannabis oil to the soybean oil also increased the induction time of oxidation at 110° C. Addition of 4.8 mg/g of cannabis oil to soybean oil with 0.5% sunflower lecithin increased the induction lime to 17.4 hours, a 5.5 hour increase over SBO=0.5% sunflower lecithin. Recall that the addition of 4.8 mg/g of cannabis oil to soybean oil increased the induction time by 2.3 hours, so this result also suggests a synergism between sunflower lecithin and cannabis oil.

A further combination of 0.01% TBHQ to the soybean oil+lecithin–cannabis oil mixtures was also conducted, and induction lime of oxidation was measured. The addition of 0.01% TBHQ to soybean oil containing 0.5% sunflower lecithin and 4.8 mg/g cannabis oil was determined to be 28.8 hours. Recall that addition of 0.01% TBHQ to soybean oil increased the induction time by 7.1 hours, the addition of sunflower lecithin increases it by 4.1 hours, and the addition of cannabis oil by 2.3 hours. The additive time on top of an induction time of oxidation for soybean oil of 7.8 hours should then be 21.7 hours. Thus, the 28.8 hours actually attained exhibits an additional 7.1 hours of stabilization. This is very significant and points to a synergistic effect between TBHQ, cannabinoids and lecithin. Similar effects were observed for TBHQ addition to soybean oil+soybean lecithin+cannabis oil.

These results are significant since they point to the added stability benefits of incorporating cannabis oil within phospholipid vesicles. Not only are they now encapsulated within a hydrophobic environment, but the environment protects the active components within the cannabis oil against oxidation, thus retaining the full dosage for commercially relevant periods of time. Additionally, cannabinoids interact synergistically with phenolic antioxidants such as tert-butyl hydroxy quinone (TBHQ), butylated hydroxy toluene (BHT), butylated hydroxyl anisole (BHA), propyl gallate (PG) and tocopherols. Addition of these to the liposomal matrix will only enhance the stability of cannabinoids further.

To confirm which of the contents are protected from oxidation, the molecular makeup of the oxidized product was analyzed. Five 1 ml chromatography glass vials were used for this purpose. 14 mg of cannabis oil were delivered into the vials from an ethanolic solution and the weight checked after evaporation of the solvent. Stock solutions of 0.5% sunflower lecithin (Sunlec25), 0.01% TBHQ and 0.5% lecithin+0.01% TBHQ were prepared. The following samples were then prepared:

A: 14 mg cannabis oil
B: 14 mg of cannabis oil+1 ml of 0.5% sunflower lecithin
C: 14 mg of cannabis oil+1 ml of 0.01% TBHQ
D: 14 mg of cannabis oil+1 ml of 0.5% sunflower lecithin+0.01% TBHQ
E: 14 mg cannabis oil The chloroform was evaporated under a stream of air until completely dry. The dry films of Samples A-D were heated for 1.5 hours at 100° C., while sample E remained at room temperature. After the heating period, samples were removed from the oven, allowed to cool to room temperature and then 1 ml of fresh chloroform was added to each vial and capped. Samples were then analyzed by gas-liquid chromatography as described previously. An Agilent 6890-series gas chromatograph (Agilent Technologies, Inc., Wilmington, DE, USA) with a 7683-series auto-sampler was used to determine the amount of X in the samples. A 15 m×0.25 mm internal diameter fused silica column with a 0.20 μm DB5 film thickness was used (Agilent Inc., USA). The oven temperature was maintained at 80° C. for 5 minutes and then programmed to increase from 80 to 300° C. at 12° C./min. The injector temperature was set at 250° C., and was operated at 19.2 psi with a hydrogen flow rate of 85 mL/min. Split ratio was set at 10:1. Helium, the earlier gas, flowed at an average velocity of 25 cm/s. A flame ionization detector was set at 350° C. with 450 mL/min air and 50 mL/min helium flowing. The separated peaks were analyzed using Open LAB software (Agilent Technologies). The amount of cannabinoid was determined by comparing retention times of the peaks to an internal standard. Tor this analysis, the main THC peak was analyzed.

Figure 22:
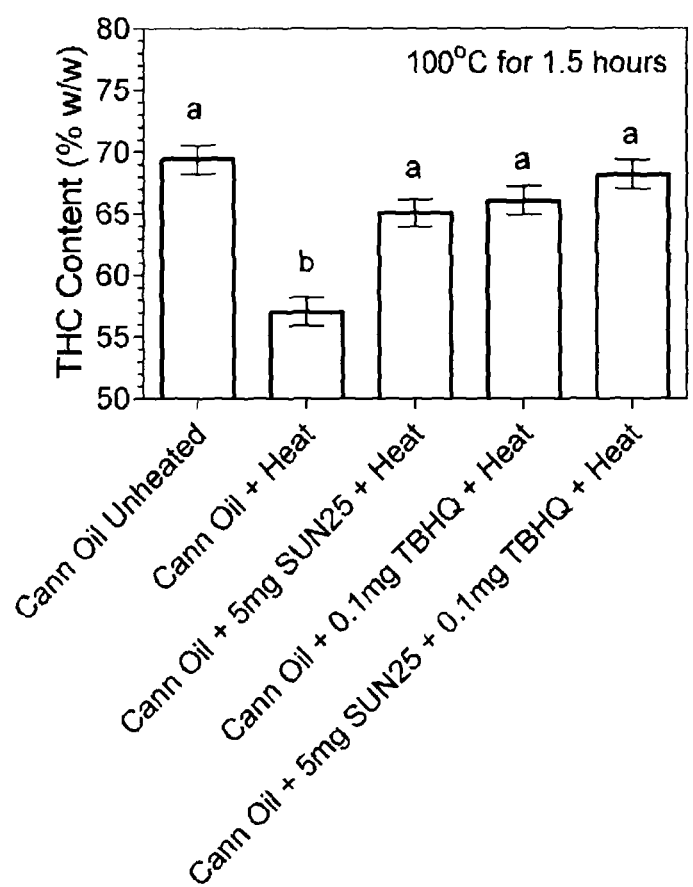
FIG. 22 graphically illustrates changes in THC relative proportion upon heating to 100° C. for 1.5 hours. Values represent means and standard deviations of two replicates. Bars with the same letter are not significantly different (P>0.05)
Figure 23:
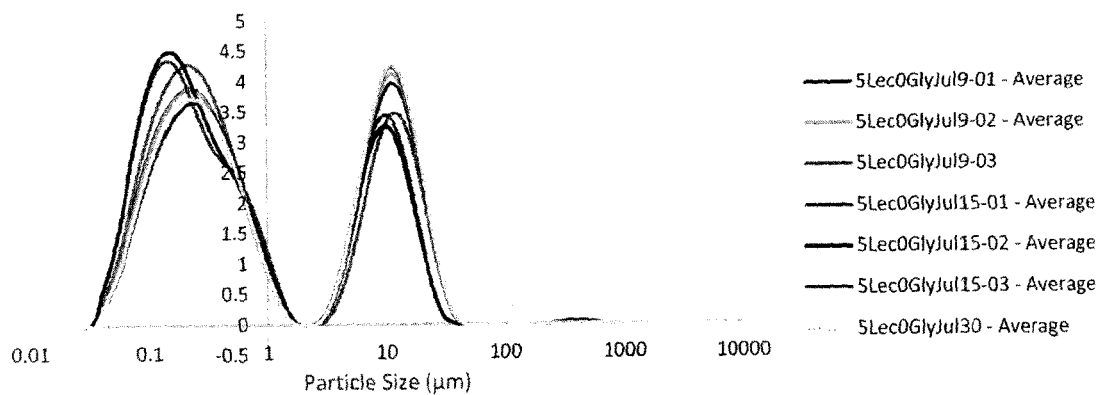
FIG. 23 illustrates the panicle size shift of GMVs to LUVs on addition of increasing amounts of glycerol from 5 to 100%.
Figure 23:
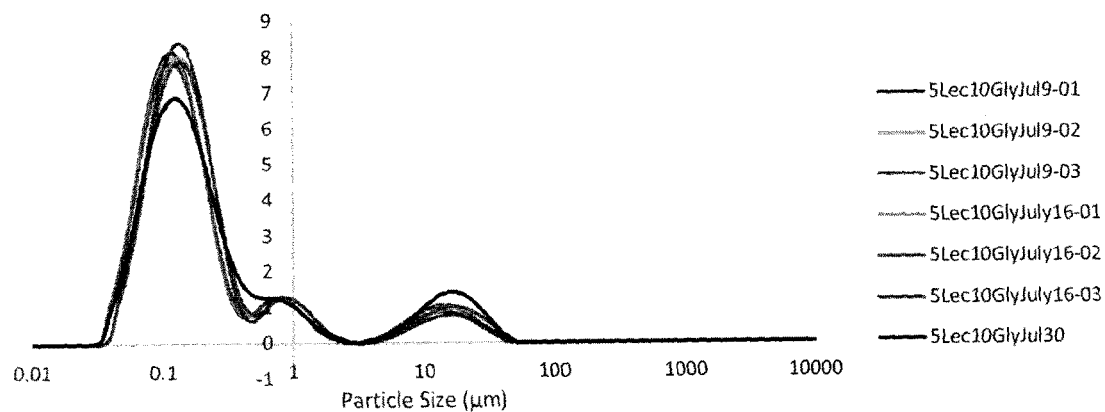
Figure 23:
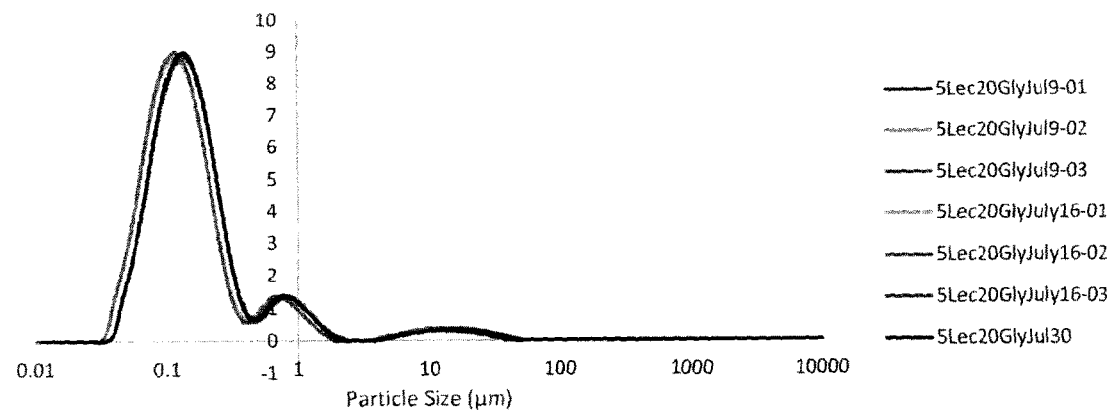

Results from this analysis are shown in FIG. 22. As can be seen, heating caused a significant degradation of THC, which was prevented by lecithin, the TBHQ and the mixture of lecithin and TBHQ. There were no differences between the antioxidant treatments in terms of preservation of THC integrity under these accelerated test conditions. This example proves that lecithin, THBQ and their mixture are acting as primary antioxidants for cannabinoids.

Example 8. Atomic Scale Molecular Mechanics Computer Simulation for the Comparison of the Cholesterol and Cannabinol A comparison of cannabinol and cholesterol was conducted to confirm the suitability of the present vesicles for loading with different cargo.

Tor these atomistic simulations, three programs were used, ChemSite Pro version 10.5 (Copyright David Michael, Ph.D)), Molecular Modelling Pro Plus (MMP+) version 8.1.40 (Norgwyn Montgomery Software Inc, James A. Quinn, lead programmer), and ChemElectrica version 3.2.12 (Norgwyn Montgomery Software Inc, James A. Quinn, lead programmer).

The structure file for cholesterol were found in ChemSite under "Lipids" while the structure file for cannabinol was found in ChemElectrica under "Narcotics". The structures were saved in a mol format and opened in MMP+. The geometry of the structures was then optimized within MMP+ using Allinger's "Standard MM2" protocol for finding the minimum energy for the structure ("Geometry Minimize"). Once the geometries were minimized, two analyses were carried out. The first was to "Calculate Dimensions" of the two molecules and the second analysis was to "Calculate Solubility Parameters". The melting points used for Cholesterol and Cannabinol were 148° C. and 77° C., respectively. A comparison of the structural characteristics of the two molecules is shown in Table 5 and the final optimized geometries in FIG. 1.

TABLE 5

Structural and chemical properties of cholesterol and cannabinol

| | Cholesterol | Cannabinol |
|---|---|---|
| Molecular Characteristic | | |
| Maximum length along x-axis (Å) | 19.9 | 17.4 |
| Maximum width above x-axis (Å) | 4.37 | 4.02 |
| Maximum width below x-axis (Å) | −4.45 | −5.72 |
| Depth in front of x-axis (Å) | 3.78 | 3.66 |
| Depth behind x-axis (Å) | −3.95 | −3.70 |
| Maximum width (perpendicular to x-axis, drawn along y-axis, Å) | 8.82 | 9.77 |
| Minimum width (any direction Perpendicular to x-axis, Å) | 7.64 | 6.48 |
| Hoy's 3-D Solubility Parameters ($J^{1/2}$ $cm^{-3/2}$) | | |
| Molar attraction function | 18.22 | 19.94 |
| Dispersion | 15.88 | 15.32 |
| Polarity | 6.39 | 8.64 |
| Hydrogen bonding | 6.24 | 9.40 |
| Molecular aggregation number | 1.13 | 1.28 |
| Energy of cohesion | 118204 | 104521 |
| Molar volume | 385.65 | 289.90 |

A cursory look at Table 5 reveals some striking similarities between the molecules. Indicated in the gray highlights are the depths (the thickness) of the molecules. These two molecules are "flat" due to their extended ring geometry and have thus one relatively long dimension, the length, an intermediate dimension, the width, and a small dimension, the depth.

However, structure/geometry is not the only consideration when comparing the partitioning behavior of these molecules into a phospholipid bilayer. Their chemical properties, in terms of solubility, should be similar as well. For this purpose, Hoy Solubility Parameters, a more theoretical version of the Hansen Solubility Parameters (Hoy, 1989) was used. Results are also shown in Table 1. Of note is the similarity in the Dispersion component of the Hoy Solubility Parameter. The environment within the fatty acid chains of a phospholipid bilayer is very nonpolar and thus its chemical properties are governed mainly by London dispersion forces. This analysis shows that both cholesterol and cannabinol have inherently similar nonpolar characteristics, which should equate to similar partitioning behaviors, or solubility, within the fatty acid chains of a phospholipid bilayer. Many of the other solubility parameters are similar as well.

This analysis confirms the uptake of molecules that exhibit appropriate structural features, i.e., si/c characteristics in specific directions, and phospholipid bilayer partitioning and solubility behavior, related to the relative balance between polar and dispersion forces, may be effectively encapsulated at high concentration by the present GMVs and LUVs Preferred cargo molecular features for encapsulation purposes include, size features such as 15-20 Angstroms in length, 6-10 Angstroms in width and 3-4 Angstroms in depth (e.g. a flat molecule). The molecule must be capable of phospholipid bilayer partitioning, having a length that is no longer than the fatty acid chains on the phospholipid a width to permit fitting between fatty acid chains. Preferred dispersion solubility is about 14-16 $J^{1/2}$ $cm^{-3/2}$ and hydrogen bonding and polarity solubility of about 6-10 $cm^{-3/2}$.

Example 9. Critical Packing Parameter of Lecithin for Vesicles

Computer simulations as described above were conduct to determine lecithin content to yield vesicles with a sufficient critical packing parameter for use to deliver cargo.

The Critical packing parameter (CPP) is a theoretical framework for determining the type of aggregation formed by surfactants (i.e. as spherical or cylindrical micelles, or vesicles, or flexible or fixed bilayers). The framework used by MMP+ is:

| CPP | Aggregation form |
|---|---|
| <0.35 | spherical micelles |
| 0.35-0.4 | spherical or cylindrical micelles |
| 0.4-0.55 | cylindrical micelles |
| 0.55-0.6 | cylindrical micelles, vesicles or flexible bilayers |
| 0.6-0.85 | flexible bilayers or vesicles |
| 0.85-0.95 | flexible bilayers |
| 0.95-1.15 | planar bilayers |
| >1.15 | inverted micelles or material is not a surfactant |

The target CPP for a vesicle is between 0.55 and ~0.85-0.95 which excludes micelles (lower) or planar bilayers (higher). The CPP for all phospholipid and fatty acid combinations was calculated according to the model:

CPP=Hydrophobic volume/(Hydrophobic length*area of the hydrophobic/hydrophilic interface) or

CPP=$V/(L*A)$.

Since the units are angstroms cubed/(angstroms squared*angstroms), CPP is unitless.

In a previous model, V was van der Waal's volume of the hydrophobic portion of the molecule (in surfactant, this usually is a hydrocarbon chain.) In the literature, V (Molecular weight/specific gravity) was used instead, giving larger numbers. To be consistent with the literature, the method of determining V was as follows:

$V$=54.6+0.124*($T$−298)+Number of $CH_2$, CH groups*(26.9+0.0146*($T$−298))−6.7 for benzene ring−0.75*(=CH carbon)

This is approximately equal to the van der Waal's volume multiplied by 1.67. T is the temperature in degrees Kelvin, and 25 C is the default temperature (Model is modified for benzene and =CH, but otherwise as in Nagarajan et al. (1991). Langmuir 1991, 7, 2934-2969).L=1.5+1.265*(longest contiguous carbon chain) (Nagarajan et al., the 1.5 accounts for the H that is found at the end of the chain in a $CH_3$ group.) Note that for double chain surfactants, L will be the same length as a single chain surfactant, but will have double the volume and often this results in surfactants that aggregate in bilayers. The calculation of the interfacial area (A) between the hydrophobic and hydrophilic portion of the surfactant is more difficult to calculate as it depends, not on geometry, but on steric and charge repulsions and interfacial tension of the hydrophobic portion of the molecule and water.

The thermodynamic model of Nagarajan et al. (1991) and Nagarajan (2001). Langmuir 2002, 18, 31-38 was used as follows. A term for the area at the interface between water and the hydrophobic portion of the molecule is referred to as interfacial repulsion (I) where: $L=$interfacial tension/$kT*(a-a_o)$, where $a_o$ is the area of the hydrophobe at the interface (V/L) and a is the area covered by the hydrophilic portion of the surfactant. If it is less than or equal to a then $l=0$ (and a is set to $a_o$; if it is larger than $a_o$ and a is set to $a_p$, the area covered by the hydrophilic part of the molecule. K is Boltzmann's constant and T is degrees Kelvin. Interfacial tension=$s_s\_s_w-2.0*psi*(s_s*s_w)^{1/2}$ where Psi=0.55, $S_s=35.0-325M^{-2/3}-0.098*(T-298)$, $S_w=72.0-0.16*(T-298)$ and M molecular weight of the hydrophobic surfactant tail. A term for the steric interactions of the hydrophilic portion of the molecule is calculated as:

$$S=-\ln(1-\lfloor a_p/a \rfloor)$$

There were also terms needed to explain charge repulsion terms between the hydrophilic head groups in the micelle, vesicle or lamellae. These terms were determined using multiple regression. The significant factors were dipole moment, distance from the hydrophilic/hydrophobic interface to the nearest formally charged atom, distance from the interface to counter-ions and distance between + and − charge in zwitterionic surfactants.

In accordance with the foregoing, CPP's for each fatly acid were determined and are shown in Table 6.

TABLE 6

| Fatty acid at sn-1 and sn-2 | Phospholipid | Critical Packing Parameter |
|---|---|---|
| Linolenic - Linolenic | Phosphatidylcholine | 0.96 |
| Linolenic-Linoleic | | 0.92 |
| Linoleic - Linoleic | | 0.84 |
| Oleic - Linoleic | | 0.85 |
| Oleic - Oleic | | 0.84 |
| Palmitic - Linoleic | | 0.79 |
| Palmitic - Oleic | | 0.80 |
| Palmitic - Palmitic | | 0.73 |
| Linolenic - Linolenic | Phosphatidylethanolamine | 1.10 |
| Linolenic-Linoleic | | 1.10 |
| Linoleic - Linoleic | | 1.00 |
| Oleic - Linoleic | | 1.01 |
| Oleic - Oleic | | 1.01 |
| Palmitic - Linoleic | | 1.03 |
| Palmitic - Oleic | | 1.01 |
| Palmitic - Palmitic | | 1.03 |
| Linolenic - Linolenic | Phosphatidylinositol | 0.77 |
| Linolenic-Linoleic | | 0.77 |
| Linoleic - Linoleic | | 0.81 |
| Oleic - Linoleic | | 0.80 |
| Oleic - Oleic | | 0.80 |
| Palmitic - Linoleic | | 0.68 |
| Palmitic - Oleic | | 0.75 |
| Palmitic - Palmitic | | 0.59 |
| | Phosphatidylserine | Protonated\|Ionized |
| Linolenic - Linolenic | | 1.14\|1.00 |
| Linolenic-Linoleic | | 1.14\|0.97 |
| Linoleic - Linoleic | | 1.16\|0.96 |
| Oleic - Linoleic | | 1.15\|0.95 |
| Oleic - Oleic | | 1.15\|0.97 |
| Palmitic - Lanoleic | | 1.14\|0.92 |
| Palmitic - Oleic | | 1.14\|0.98 |
| Palmitic - Palmitic | | 1.10\|0.97 |
| Linolenic - Linolenic | Phosphatidic Acid | 0.89 |
| Linolenic-Linoleic | | 0.88 |

TABLE 6-continued

| Fatty acid at sn-1 and sn-2 | Phospholipid | Critical Packing Parameter |
|---|---|---|
| Linoleic Linoleic | | 0.84 |
| Oleic - Linoleic | | 0.84 |
| Oleic - Oleic | | 0.84 |
| Palmitic - Linoleic | | 0.88 |
| Palmitic - Oleic | | 0.93 |
| Palmitic - Palmitic | | 0.94 |
| Linolenic - Linolenic | Phosphatidylglycerol | 0.60 |
| Linolenic-Linoleic | | 0.60 |
| Linoleic - Linoleic | | 0.58 |
| Oleic - Linoleic | | 0.58 |
| Oleic - Oleic | | 0.60 |
| Palmitic - Linoleic | | 0.56 |
| Palmitic - Oleic | | 0.56 |
| Palmitic - Palmitic | | 0.56 |
| LnPC2/LnPC1 | Lyso-Phosphatidylcholine | 0.20/0.21 |
| LPC2/LPC1 | | 0.20/0.22 |
| OPC2/OPC1 | | 0.23/0.23 |
| PPC2/PPC1 | | 0.20/0.22 |
| LnPE2/LnPE1 | Lyso- Phosphatidylethanolamine | 0.46/0.45 |
| LPE2/LPE1 | | 0.47/0.46 |
| OPE2/OPE1 | | 0.46/0.46 |
| PPE2/PPE1 | | 0.45/0.44 |
| LnPI2/LnPI1 | Lyso-Phosphatidylinositol | 0.060/0.090 |
| LPI2/LPI1 | | 0.060/0.092 |
| OPI2/OPI1 | | 0.064/0.092 |
| PPI2/PPI1 | | 0.064/0.100 |
| | Lyso-Phosphatidylserine | Protonated\|Ionized |
| LnPS2/LnPS1 | | 0.33/0.30\|0.25/0.22 |
| LPS2/LPS1 | | 0.36/0.36\|0.20/0.28 |
| OPS2/OPS1 | | 0.31/0.31\|0.25/0.25 |
| PPS2/PPS1 | | 0.30/0.32\|0.27/0.26 |
| LnPA2/LnPA1 | Lyso-Phosphatidic Acid | 0.46/0.44 |
| LPA2/LPA1 | | 0.42/0.40 |
| OPA2/OPA1 | | 0.40/0.40 |
| PPA2/PPA1 | | 0.39/0.38 |

PC, PI, PA and PG exhibit CPP within the target range, while PE has a CPP above the target range. The ratio of PC+PA+PI/PE was calculated for soybean, sunflower seed and rapeseed lecithin as shown in Table 7. Preferably, the ratio of PC+PA+PI:PE is at least 2, and more preferably, greater than 3 or 4.

TABLE 7

| Composition (wt %) of phosphatides of various lecithins | | | |
|---|---|---|---|
| Phosphatide | Soybean | Sunflower seed | Rapeseed |
| PC | 32 | 34 | 37 |
| PE | 23 | 17 | 20 |
| PI | 21 | 30 | 22 |
| PA | 8 | 6 | 8 |
| Others | 15 | 13 | 13 |
| (PC + PI + PA)/PE | 2.65 | 4.11 | 3.35 |

A ratio of PC+PI+PA to PE of greater than 2.5, preferably greater than 3 or 4 is desirable. Thus, sunflower lecithin is superior since this ratio is above 4.

The type of fatly acid in the lecithin also plays a role as shown in Table 8. Fatly acids, 18:2, 18:1 and combinations appear desirable, while 18:3 (Ln) is not desirable. Palmitic (16:0) may be acceptable however, fluid fatty acid with no phase transition was desirable.

TABLE 8

Fatty acid compositions of vegetable lecithins and oils

| Fatty acid | Soybean Lecithin | Soybean Oil | Sunflower seed Lecithin | Sunflower seed Oil | Rapeseed Lecithin | Rapeseed Oil |
|---|---|---|---|---|---|---|
| 16:0 | 16 | 11 | 11 | 7 | 7 | 4 |
| 18:0 | 4 | 4 | 4 | 5 | 1 | 2 |
| 18:1 | 17 | 23 | 18 | 29 | 56 | 61 |
| 18:2 | 55 | 54 | 63 | 58 | 25 | 22 |
| 18:3 | 7 | 8 | 0 | 0 | 6 | 10 |
| Others | 1 | 0 | 4 | 1 | 5 | 1 |

Example 10. Preparation of LUVs from GMVs

A novel method of preparing large unilamellar vesicles (LUVs) from giant multilamellar vesicles (GMV) without homogenization was developed.

Methods

Spontaneous lecithin vesicles were prepared by combining lecithin with water and glycerol. All samples were prepared using 5% (wt/wt) soy lecithin in a water-glycol mixture, e.g. lecithin-glycerol, lecithin-ethylene glycol and lecithin-propylene glycol, respectively. Water-glycerol mixtures were prepared in 10% increments from 0-100% glycerol in water.

A water bath attached to a benchtop paddle mixer chamber was preheated to 60° C. All material components were measured on a percent weight basis. Glycerol and water were measured in the corresponding ratios and poured into the preheated chamber, the paddle mixer was inserted, and the lid was placed on the chamber. The paddle mixer was operated at 400 rpm. After 5 minutes, the lid was removed, the soy lecithin was added to the mixing chamber, the lid was replaced, and the sample was stirred for four hours. The lid and paddle were removed, and samples were poured into sealable containers for storage. Diluted samples were prepared from premade samples. Samples were diluted using a 1:1 ratio of sample to water. Water was added to a given quantity of sample and mixed slowly by hand for three minutes.

Mastersizer: A Mastersizer 2000 (Malvern Pananalytical, Malvern. UK) light scattering device was used to determine particle sizes within a mixture immediately following mixing, and once per week for 3 weeks following sample creation. The Mastersizer dispersion chamber was set to 1200 rpm, several drops of sample were added to the chamber and three measurements were taken and averaged.

Water Activity: The water activity machine (Aqualab Dew Point Water Activity Meter 4TEV, METER Food, Pullman, WA USA) was calibrated using known standards. Samples were cooled to room temperature. Following calibration, water activity of the samples was measured. 3 measurements were taken, and the water activity machine was given 5 minutes to reach a steady state measurement. An average value was then calculated form these results.

Results

The data shows that when glycerol is combined with spontaneous liposomes (GMV) prepared in distilled water in an amount of 10-90% glycerol, they exhibit a change in size from about 10 microns to 100 nm without any homogenization (Table 9 and FIGS. 23(A)-(K)). In preparing the liposomes, lecithin may be combined with water to which the glycerol was added, or may be combined with glycerol (super viscous) to which water was added. In either case, small multilamellar vesicles resulted.

TABLE 9

| | Water Activity | D [3, 2] nm |
|---|---|---|
| 5Lec100Gly Jul 12 | 0.16 | 10.089 |
| 5Lec100Gly Jul 19 | | 8.040 |
| 5Lec100Gly Jul 16 | | 245 |
| 5Lec100GlyJul 30 | | 8.455 |
| 5Lec90Gly Jul 12 | 0.22 | 212 |
| 5Lec90Gly Jul 19 | | 216 |
| 5Lec90GlyJul 30 | | 208 |
| 5Lec80Gly Jul 12 | 0.26 | 216 |
| 5Lec80Gly Jul 19 | | 180 |
| 5Lec80GlyJul 30 | | 173 |
| 5Lec70Gly Jul 3 | 0.53 | 132 |
| 5Lec70Gly Jun 26 | | 126 |
| 5Lec70Gly Jul 9 | | 129 |
| 5Lec70GlyJul 30 | | 129 |
| 5Lec60Gly Jul 3 | 0.66 | 143 |
| 5Lec60Gly Jun 26 | | 142 |
| 5Lec60Gly Jul 9 | | 140 |
| 5Lec60Gly Jul 19 | | 130 |
| 5Lec60GlyJul 30 | | 126 |
| 5Lec50Gly Jul 3 | 0.78 | 125 |
| 5Lec50Gly Jul 9 | | 123 |
| 5Lec50Gly0.1 mM Jul 12 | | 142 |
| 5Lec50GlyJul30 | | 128 |
| 5Lec40Gly Jul 3 | 0.84 | 125 |
| 5Lec40Gly Jul 9 | | 124 |
| 5Lec40GlyJul30 | | 123 |
| 5Lec30Gly Jul 9 | 0.91 | 127 |
| 5Lec30Gly Jul 16 | | 135 |
| 5Lec30GlyJul30 | | 203 |
| 5Lec20Gly Jul 9 | 0.94 | 120 |
| 5Lec20Gly Jul 13 | | 121 |
| 5Lec20Gly Jul 30 | | 120 |
| 5Lec10Gly Jul 9 | 0.98 | 133 |
| 5Lec10Gly Jul 16 | | 132 |
| 5Lec10Gly Jul 30 | | 152 |
| 5Lec0Gly Jul 9 | 0.99 | 284 |
| 5Lec0Gly Jul 15 | | 237 |
| 5Lec0GlyJul 30 | | 317 |

The resulting vesicles are large unilamellar vesicles.

It is noted that the addition of glycerol reduces the water activity. As glycerol is increased, the water activity deceases. Preparations including more than 40% glycerol exhibit a water activity that would not support bacterial growth, i.e. a water activity of less than 0.85. Therefore, such preparations will have an extended shelf life.

Liposomes were similarly prepared with a 1:1 dilution of ethylene glycol and a 1:1 dilution of propylene glycol which resulted in a decrease in particle size of a portion of the liposomes.

REFERENCES

Allen, T. M. and Cullis, P. R. 2013. Liposomal drug delivery systems: from concept to clinical applications. Advanced drug delivery reviews 65: 36-48

Bangham, A. and Horne, R. W. 1964. Negative staining of phospholipids and their structural modification by surface-active agents as observed in the electron microscope. J. Molecular Biology 8: 660-668

Bligh, F G. and Dyer, W. J. 1959. A rapid method of total lipid extraction and purification. Canadian Journal of Biochemistry and Physiology 37: 911-917

Bozzuto, G. and Molinari, A. 2015. Liposomes as nanomedical devices. International Journal of Nanomedicine 10: 975-999

Cullis, P. R., Hope, M. J. and Tilcock, C. P. S. 1986. Lipid polymorphism and the roles of lipids in membranes. Chemistry and Physics of Lipids 40: 127-144

Demel, R. A., Jansen, J. W. C. M., van Dijck, P. W. M. and van Deenen, L. L. M. 1977. The preferential interactions of cholesterol with different classes of phospholipids. Biochimica et Biophysica Acta 465: 1-10

Epand, R. M., Bach, D., and Wachel, E. 2016. In vitro determination of the solubility limit of cholesterol in phospholipid bilayers. Chemistry and Physics of Lipids 199: 3-10

Frolov, V., Shnyrova, A. V. and Zimmerberg, J. 2011. Lipid Polymorphisms and Membrane Shape. Cold Spring Harbor Perspectives in Biology 3:a004747

Goldfine, H. 1984 Bacterial membranes and lipid packing theory. Journal of Lipid Research 25: 1501-507

Guida, V. 2010. Thermodynamics and kinetics of vesicles formation process Advances in Colloid and Interface Science 161: 77-88

Helfrich, W. 1973. Elastic properties of lipid bilayers: theory and possible experiments. Z. Naturforschung 28 c: 693-703.

Hope, M. J., Bally, M. B., Mayer, L. D., Janoff, A. S. and Cullis, P. R. 1986. Generation of multilamellar and unilamellar phospholipid vesicles. Chemistry and Physics of Lipids 40: 89-107

Hoy, K. L. 1989. Solubility Parameter as a Design Parameter for Water Borne Polymers and Coatings. Journal of Coated Fabrics 19:53-67

Israelachvilli, J. 1992. Intermolecular & Surface Forces. Academic Press, N.Y. pp 450.

Lasic, D. D. 1988a. The mechanism of vesicle formation. Biochemical Journal 259:1-11

Lasic, D. D. 1988b. On the thermodynamic stability of liposomes. Journal of Colloid and Interface Science 140: 302-304

Olson, K, Hunt, C. A., Szoka, P. C., Vail, W. J. and Papahadjopoulos, D. 1979. Preparation of liposomes of defined size distribution by extrusion through polycarbonate membranes. Biochimica and Biophysica Acta 557: 9-23

Safran, S. A., Pincus, P., and Andelman, D. 1990. Theory of spontaneous vesicle formation in surfactant mixtures. Science 248: 354-356

Safran, S. A., Pincus, P., and Andelman, D. and MacKintosh, F. C. 1991. Stability and phase behavior or mixed surfactant vesicles. Physical Review A 43: 1071-1078.

Tillock, C. P. S. 1986. Lipid polymorphism. Chemistry and Physics of Lipids 40: 109-125 van Dijek, P. W. M, de Druijff, B., van Deenen, L. L. M., de Gier, J and Demel, R. A. 1976. The preference of cholesterol for phosphatidylcholine in mixed phospatidylcholine-phosphatidylethanolamine bilayers. Biochimica Biophysica Acta 455: 576-587

Wattenberg, B. W. and Silbert, D. F. 1983. Sterol partitioning among intracellular membranes. J. Biological Chemistry 258: 2284-2289

Wang, F. C., Acevedo, N.C., Marangoni, A. G. 2017. Food and Function 8: 3964-3969

Woodle, M. C. and Paphadjopoulos, D. 1989. Liposome preparation and size characterization. Methods in Enzymology 171: 193-217

Zetzl, A., Ollivon, M., Marangoni, A. 2009. A coupled differential scanning calorimetry and X-ray study of the mesomorphic phases of monostearin and stearic acid in water. Crystal Growth and Design 9: 3928-3933

The invention claimed is:

1. Large unilamellar vesicles having a size in the range of about 100-400 nm consisting essentially of a combination and admixture of lecithin and a polyol in an aqueous buffer, wherein said vesicles have a water activity of less than 0.9.

2. The unilamellar vesicles of claim 1, wherein the lecithin is deoiled lecithin.

3. The unilamellar vesicles of claim 1, wherein the lecithin comprises phosphatidylcholines in an amount in the range of about 15-50% by wt, phosphatidylethanolamines in an amount in the range of about 5-25 wt % and phosphatidic acids in an amount of less than 10% by wt.

4. The unilamellar vesicles of claim 1, wherein the polyol is glycerol.

5. The unilamellar vesicles of claim 1, comprising cargo.

6. The unilamellar vesicles of claim 1, having a water activity of less than 0.85.

7. The unilamellar vesicles of claim 5, wherein the cargo is hydrophilic.

8. The unilamellar vesicles of claim 5, wherein the cargo is hydrophobic.

9. A method of making large unilamellar vesicles as defined in claim 1 comprising the step of mixing without homogenization giant multi-lamellar vesicles (GMVs) in the size range of 3-10 μm consisting essentially of lecithin with a low molecular weight polyol in an aqueous buffer for a sufficient period of time.

10. The method of claim 9, wherein the polyol is glycerol.

11. The method of claim 9, wherein the polyol is used in an amount of 10-90% by wt.

12. The method of claim 9, wherein the vesicles are reduced to a size within the range of 50 to 400 nm.

13. The method of claim 12, wherein the vesicles are reduced to a size within the range of 50-150 nm.

14. The method of claim 9, wherein the vesicles exhibit a water activity of less than 0.85.

15. The method of claim 9, wherein the lecithin is deoiled lecithin.

16. The method of claim 9, wherein the lecithin comprises phosphatidylcholines in an amount in the range of about 15-50% by wt, phosphatidylethanolamines in an amount in the range of about 5-25 wt % and phosphatidic acids in an amount of less than 10% by wt.

17. The method of claim 11, wherein the polyol is used in an amount of greater than 30% by wt.

18. The method of claim 11, wherein the polyol is glycerol and is used in an amount of 40-90% by wt.

* * * * *